(12) United States Patent
Cui et al.

(10) Patent No.: US 12,194,201 B2
(45) Date of Patent: Jan. 14, 2025

(54) SILICA NANOPARTICLE DOPED CONDUCTIVE POLYMER

(71) Applicant: University of Pittsburgh—Of the Commonwealth System of Higher Education, Pittsburgh, PA (US)

(72) Inventors: Xinyan Cui, Wexford, PA (US); Kevin M. Woeppel, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1186 days.

(21) Appl. No.: 16/984,042

(22) Filed: Aug. 3, 2020

(65) Prior Publication Data

US 2021/0038773 A1 Feb. 11, 2021

Related U.S. Application Data

(60) Provisional application No. 62/884,047, filed on Aug. 7, 2019.

(51) Int. Cl.
*A61B 5/25* (2021.01)
*A61B 5/145* (2006.01)
(Continued)

(52) U.S. Cl.
CPC ........ *A61L 31/128* (2013.01); *A61B 5/14532* (2013.01); *A61B 5/14865* (2013.01);
(Continued)

(58) Field of Classification Search
CPC .... A61L 31/128; A61L 31/16; A61L 2420/04; A61L 31/14; A61L 2400/12; A61L 31/10;
(Continued)

(56) References Cited

U.S. PATENT DOCUMENTS

2008/0097280 A1* 4/2008 Martin ................. A61K 9/0009
604/21
2017/0326381 A1* 11/2017 Kozai .................. A61N 1/0551
(Continued)

FOREIGN PATENT DOCUMENTS

AU 2018308332 A1 * 3/2020 ........... A61K 31/203
KR 20050055202 A * 6/2005 ........... G01N 27/327
(Continued)

OTHER PUBLICATIONS

Seth J. Wilks1 Sarah M. Richardson-Burns2,3 Jeffrey L. Hendricks3,4 David C. Martin2,3,4 Kevin J. Otto1,5, Jun. 9, 2009, Front. Neuroeng, vol. 2, "Poly(3,4-ethylenedioxythiophene) as a micro-neural interface material for electrostimulation" (Year: 2009).*

(Continued)

*Primary Examiner* — Eun Hwa Kim
*Assistant Examiner* — Ana Veruska Guerrero
(74) *Attorney, Agent, or Firm* — Klarquist Sparkman, LLP

(57) ABSTRACT

Disclosed herein are embodiments of a conductive polymer doped with silica nanoparticles. In several embodiments, a coated electrode comprising a coating of the conductive polymer on a conductive surface of the electrode is provided. In some embodiments, the silica nanoparticles of the conductive polymer are mesoporous and are loaded with a pharmaceutical agent. Methods of using the conductive polymer doped with silica nanoparticles are also provided, including methods of recording or stimulating a bioelectric signal and methods of administering a pharmaceutical agent to a subject.

30 Claims, 17 Drawing Sheets
(13 of 17 Drawing Sheet(s) Filed in Color)

(51) Int. Cl.

| | |
|---|---|
| *A61B 5/1486* | (2006.01) |
| *A61B 5/291* | (2021.01) |
| *A61B 5/296* | (2021.01) |
| *A61L 31/12* | (2006.01) |
| *A61L 31/16* | (2006.01) |
| *A61N 1/05* | (2006.01) |
| *A61N 1/36* | (2006.01) |
| *A61N 1/362* | (2006.01) |
| *A61N 1/39* | (2006.01) |
| *A61B 5/262* | (2021.01) |
| *A61B 5/263* | (2021.01) |
| *A61B 5/283* | (2021.01) |

(52) U.S. Cl.
CPC ............... *A61B 5/25* (2021.01); *A61B 5/291* (2021.01); *A61B 5/296* (2021.01); *A61L 31/16* (2013.01); *A61N 1/0502* (2013.01); *A61N 1/0534* (2013.01); *A61N 1/0541* (2013.01); *A61N 1/0551* (2013.01); *A61N 1/36007* (2013.01); *A61N 1/36038* (2017.08); *A61N 1/362* (2013.01); *A61N 1/3962* (2013.01); *A61B 5/262* (2021.01); *A61B 5/263* (2021.01); *A61B 5/283* (2021.01); *A61B 2562/0209* (2013.01); *A61B 2562/125* (2013.01); *A61B 2562/14* (2013.01); *A61L 2420/04* (2013.01)

(58) Field of Classification Search
CPC ... A61B 5/14532; A61B 5/14865; A61B 5/25; A61B 5/291; A61B 5/296; A61B 5/262; A61B 5/263; A61B 5/283; A61B 2562/0209; A61B 2562/125; A61B 2562/14; A61B 5/268; A61B 5/28; A61N 1/0502; A61N 1/0534; A61N 1/0541; A61N 1/0551; A61N 1/36007; A61N 1/36038; A61N 1/362; A61N 1/3962
See application file for complete search history.

(56) References Cited

U.S. PATENT DOCUMENTS

| | | | |
|---|---|---|---|
| 2018/0333571 A1* | 11/2018 | Pepin | A61N 1/0556 |
| 2020/0178864 A1 | 6/2020 | Cui et al. | |
| 2021/0260534 A1* | 8/2021 | Newbloom | C25B 13/04 |

FOREIGN PATENT DOCUMENTS

| | | | | |
|---|---|---|---|---|
| WO | WO-2005082277 A1 * | 9/2005 | ........... | A61K 31/337 |
| WO | WO-2007028003 A2 * | 3/2007 | ............... | A61B 5/04 |
| WO | WO-2018009924 A1 * | 1/2018 | ........... | C07D 495/04 |

OTHER PUBLICATIONS

Abidian et al., "Conducting-Polymer Nanotubes for Controlled Drug Release," *Adv Mater* 18.4: 405-409, Feb. 2006.

Bertrand et al., "Double-Blind Study of the Safety of Clopidogrel with and without a Loading Dose in Combination with Aspirin Compared with Ticlopidine in Combination with Aspirin after Coronary Stenting: The Clopidogrel Aspirin Stent International Cooperative Study," *Circulation* 102.6: 624-629, Aug. 2000.

Catt et al., "Self-Powered Therapeutic Release from Conducting Polymer/Graphene Oxide Films on Magnesium," *Nanomedicine* 14.7: 2495-2503, Oct. 2018.

Chen et al., "Recent Advances in Electrochemical Sensing for Hydrogen Peroxide: A Review," *Analyst* 137.1: 49-58, Jan. 2012.

Cogan et al., "In Vitro Comparison of the Charge-Injection Limits of Activated Iridium Oxide (AIROF) and Platinum-Iridium Mircoelectrodes," *IEEE Trans Biomed Eng.* 52.9: 1612-1614, Sep. 2005.

Collinger et al., "7 Degree-of-Freedom Neuroprosthetic Control by an Individual with Tetraplegia," *Lancet* 381.9866: 557-564, Feb. 2013.

Du et al., "Electrically Controlled Neurochemical Release from Dual-Layer Conducting Polymer Films for Precise Modulation of Neural Network Activity in Rat Barrel Cortex," *Adv Funct Mater.* 28.12: 1703988, Mar. 2018.

Flesher et al., "Intracortical Microstimulation of Human Somatosensory Cortex," *Sci Trans Med* 8.361: 361ra141, Oct. 2016.

Golabchi et al., "Melatonin Improves Quality and Longevity of Chronic Neural Recording," *Biomaterials* 180: 225-239, Oct. 2018.

Gomez and Schmidt, "Nerve Growth Factor-Immobilized Polypyrrole: Bioactive Electrically Conducting Polymer for Enhanced Neurite Extension," *J Biomed Mater Res A.* 81.1: 135-149, Apr. 2007.

Guimard et al., "Conducting Polymers in Biomedical Engineering," *Prog Polym Sci.* 32: 876-921, 2007.

Gulcin et al., "On the In Vitro Antioxidative Properties of Melatonin," *J Pineal Res.* 33.3: 167-171, Oct. 2002.

Gupta et al., "Silica Functionalized Sulfonic Acid Catalyzed One-Pot Synthesis of 4,5,8a-triarylhex-ahydropyrimido[4,5-d]pyrimidine-2,7(1H,3 H)-diones under Liquid Phase Catalysis," *J Braz Chem Soc.* 21.2: 349-354, 2010.

Harish et al., "Barrier Films to Control Loss of 9,10-anthraquinone-2-sulphonate Dopant from PEDOT Films during Electrochemical Transitions," *Electrochimica Acta* 54: 3618-3622, 2009.

He and Shi, Mesoporous Silica Nanoparticle Based Nano Drug Delivery Systems: Synthesis, Controlled Drug Release and Delivery, Pharmacokinetics and Biocompatibility, *J Mater Chem.* 21: 5845-5855, 2011.

Hernandez et al., "Template Fabrication of Protein-Functionalized Gold-Polypyrrole-Gold Segmented Nanowires," *Chem Mater.* 16: 3431-3438, 2004.

King et al., "Structural, Chemical and Electrochemical Characterization of poly(3,4-ethylenedioxythiophene) (PEDOT) Prepared with Various Counter-Ions and Heat Treatments," *Polymer (Guildf)* 52.5: 1302-1308, Mar. 2011.

Kozai et al., "Chronic In Vivo Evaluation of PEDOT/CNT for Stable Neural Recordings," *IEEE Trans Biomed Eng.* 63.1: 111-119, Jan. 2016.

Kozai et al., "Ultrasmall Implantable Composite Microelectrodes with Bioactive Surfaces for Chronic Neural Interfaces," *Nat Mater.* 11.12: 1065-1073, Dec. 2012.

Kum et al., "Biomolecules-Carbon Nanotubes Doped Conducting Polymer Nanocomposites and Their Sensor Application," *Talanta* 74.3: 370-375, Dec. 2007.

Lai et al., "A Mesoporous Silica Nanosphere-Based Carrier System with Chemically Removable CdS Nanoparticle Caps for Stimuli-Responsive Controlled Release of Neurotransmitters and Drug Molecules," *J Am Chem Soc.* 125.15: 4451-4459, Apr. 2003.

Lee et al., "Simple Synthesis of Functionalized Superparamagnetic Magnetite/Silica Core/Shell Nanoparticles and their Application as Magnetically Separable High-Performance Biocatalysts," *Small* 4.1: 143-152, Jan. 2008.

Leon et al., "A Clinical Trial Comparing Three Antithrombotic-Drug Regimens After Coronary-Artery Stenting. Stent Anticoagulation Restenosis Study Investigators," *N Engl J Med.* 339.23: 1665-1671, Dec. 1998.

Ludwig et al., "Poly(3,4-ethylenedioxythiophene) (PEDOT) Polymer Coatings Facilitate Smaller Neural Recording Electrodes," *J Neural Eng.* 8.1: 014001, Feb. 2011 (14 pages).

Luo and Cui, "Electrochemically Controlled Release Based on Nanoporous Conducting Polymers," *Electrochemistry Communications* 11.2: 402-404, Feb. 2009.

Luo et al., "Highly Stable Carbon Nanotube Doped poly(3,4-ethylenedioxythiophene) for Chronic Neural Stimulation," *Biomaterials* 32.24: 5551-5557, Aug. 2011.

Pickup et al., "In Vivo Molecular Sensing in Diabetes Mellitus: An Implantable Glucose Sensor with Direct Electron Transfer," *Diabetologia* 32.3: 213-217, 1989.

Proctor et al., "Electrophoretic Drug Delivery for Seizure Control," *Sci Adv.* 29.4: eaau1291, Aug. 2018 (8 pages).

(56) References Cited

OTHER PUBLICATIONS

Simon et al., "Organic Electronics for Precise Delivery of Neurotransmitters to Modulate Mammalian Sensory Function," *Nat Mater* 8.9: 742-746, Sep. 2009.
Stauffer and Cui, "Polyprrole Doped with 2 Peptide Sequences from Laminin," *Biomaterials* 27.11: 2405-2413, Apr. 2006.
Thompson et al., "Effect of the Dopant Anion in Polypyrrole on Nerve Growth and Release of a Neurotrophic Protein," *Biomaterials* 32.15: 3822-3831, May 2011.
Venkatraman et al., "In Vitro and in Vivo Evaluation of PEDOT Microelectrodes for Neural Stimulation and Recording," *IEEE Trans Neural Syst Rehabil Eng.* 19.3: 307-316, Jun. 2011.
Vlamidis et al., "Electrodeposition of PEDOT Perchlorate as an Alternative Route to PEDOT:PSS for the Development of Bulk Heterojunction Solar Cells," *J Solid State Electrochem* 19: 1685-1693, 2015.
Wadhwa et al., "Electrochemically Controlled Release of Dexamethasone from Conducting Polymer Polypyrrole Coated Electrode," *J Control Release* 110.3: 531-541, Feb. 2006.
Weaver et al., "Electrically Controlled Drug Delivery from Graphene Oxide Nanocomposite Films," *ACS Nano* 8.2: 1834-1843, Feb. 2014.
Woeppel et al., "Enhancing Surface Immobilization of Bioactive Molecules via a Silica Nanoparticle Based Coating," *J Mater Chem B.* 6.19: 3058-3067, May 2018.
Woeppel et al., "Recent Advances in Neural Electrode-Tissue Interfaces," *Curr Opin Biomed Eng.* 4: 21-31, Dec. 2017.
Zheng et al., "Soft Conducting Elastomer for Peripheral Nerve Interface," *Adv Healthc Mater.* 8.9: e1801311, May 2019.

\* cited by examiner

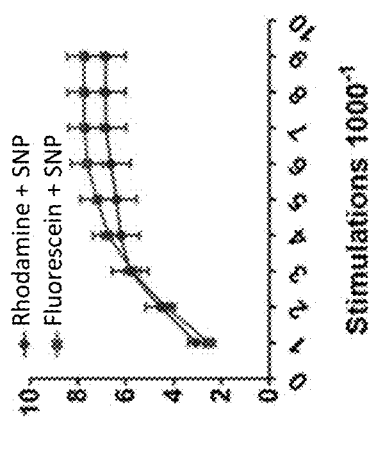
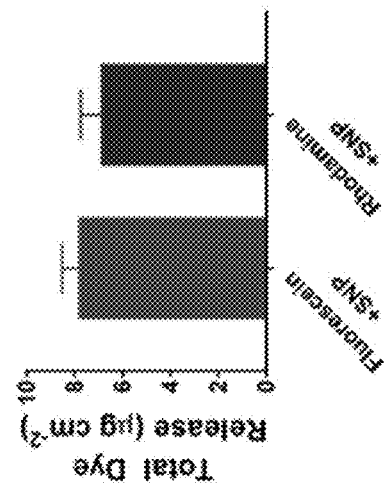
FIG. 6A
FIG. 6B
FIG. 6C
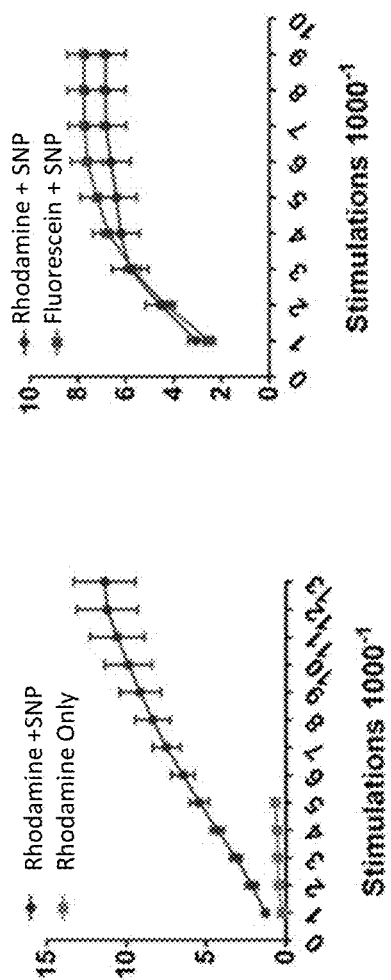
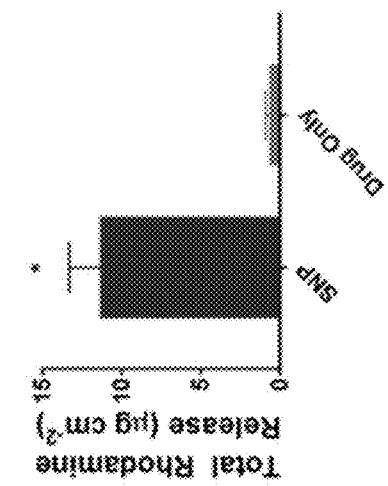
FIG. 6D
FIG. 6E
FIG. 6F
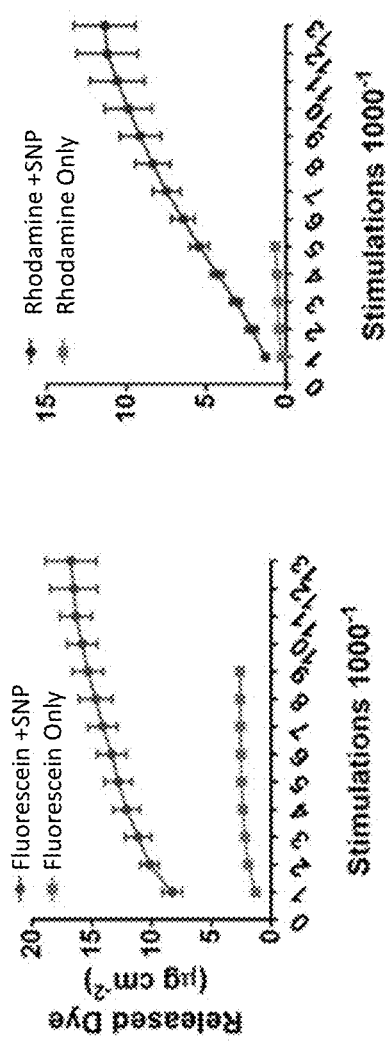
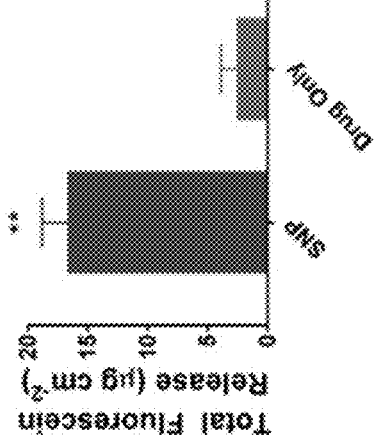

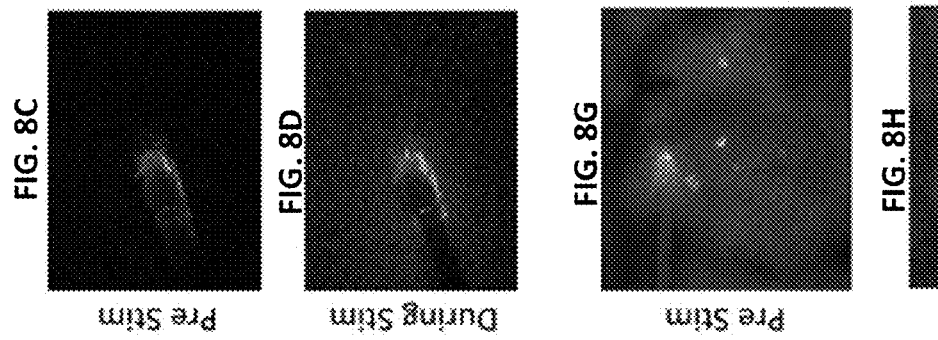
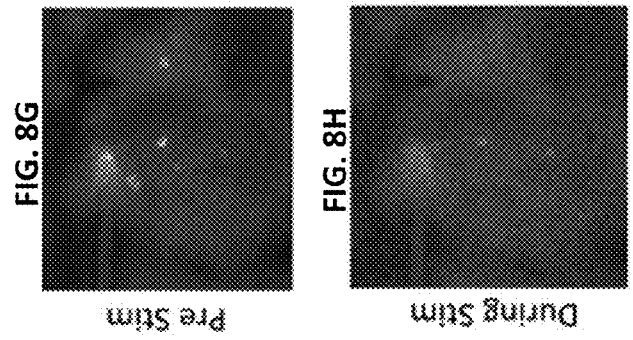
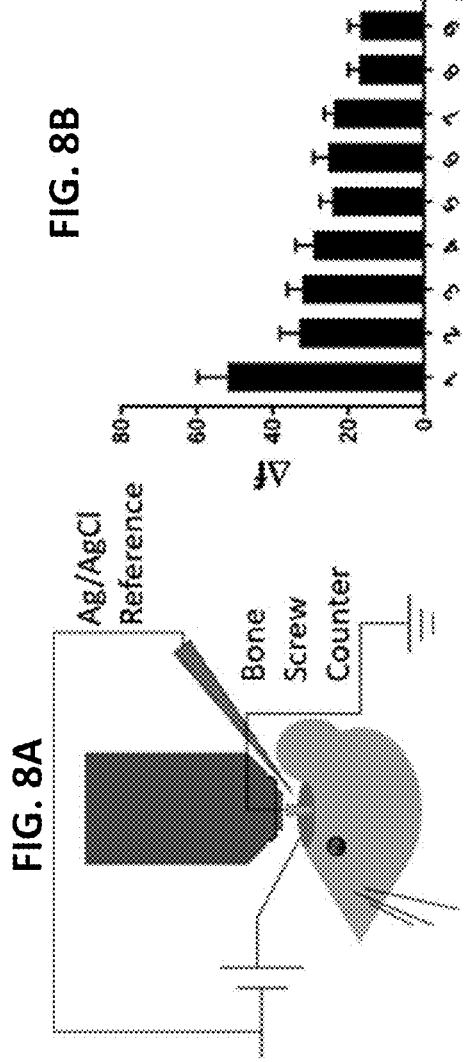
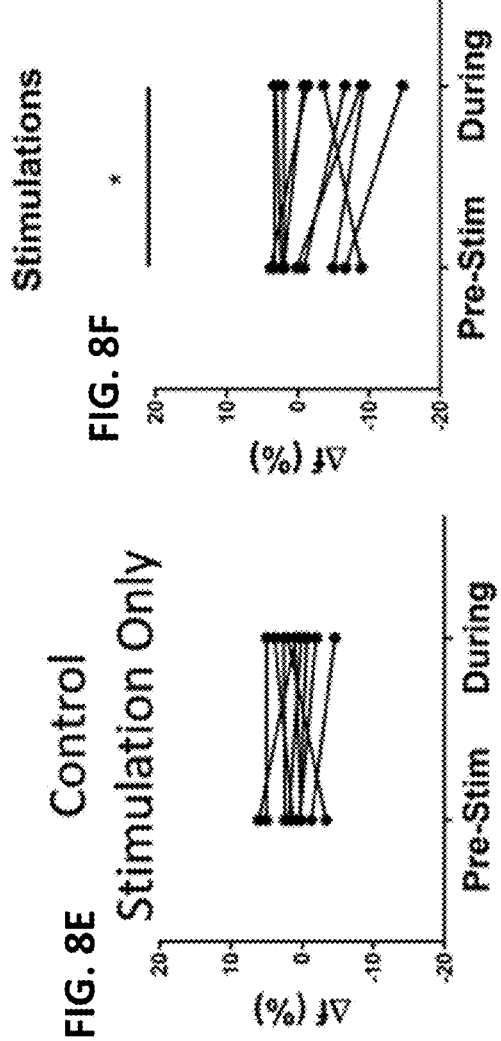

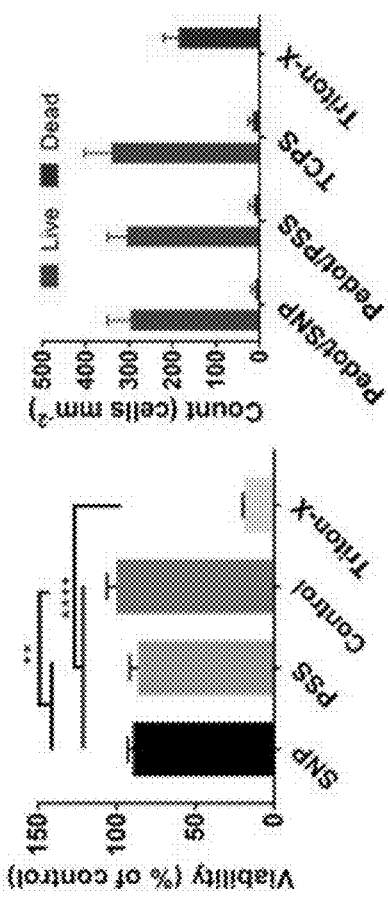
FIG. 10A
FIG. 10B
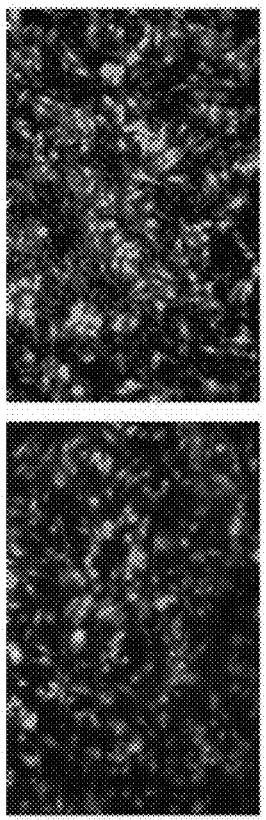
FIG. 10C
FIG. 10E
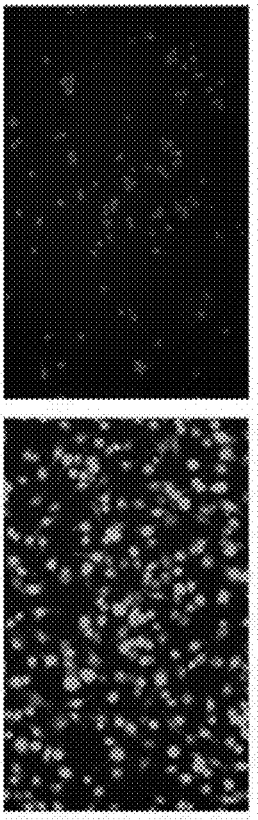
FIG. 10D
FIG. 10F

SILICA NANOPARTICLE DOPED CONDUCTIVE POLYMER

CROSS REFERENCE TO RELATED APPLICATION

This application claims priority to U.S. Provisional Application No. 62/884,047, filed Aug. 7, 2019, the contents of which are hereby incorporated by reference in their entirety.

ACKNOWLEDGMENT OF GOVERNMENT SUPPORT

This invention was made with government support under Grant Nos. NS062019, NS089688, and NS110564 awarded by the National Institutes of Health. The government has certain rights in the invention.

FIELD

The present disclosure relates to the field of coated electrodes for medical and bio-medical use.

BACKGROUND

Biomedical electrodes are a primary component of many medical devices, including cardiac pacemakers and defibrillators, deep brain stimulation devices, cochlear implants, peripheral nerve stimulation devices, spinal cord stimulation devices for pain management, and diagnostic tools. The electrode(s) found on the tip of biomedical leads are placed in contact with the appropriate target tissue, and are used to transmit bio-electrical signals to and from the device and target tissue.

However, it has become increasingly apparent that material limitations are impeding progress in the development of next generation devices. While electrode miniaturization is desired for reducing invasiveness and increasing information flow density, it poses significant challenges to material properties and stability, as both impedance and charge injection limits are inversely proportional to the surface area of the electrode. One potential solution is to modify the surface with conducting polymers. These intrinsically conductive coatings have the ability to greatly increase charge injection limits for safe and efficacious stimulation and maintain low impedances necessary to record bio-electric signals.

SUMMARY

Provided herein are embodiments of a conductive polymer doped with negatively charged silica nanoparticles and uses thereof. Combining the unique properties of conducting polymers with a nanoparticle dopant produces a highly tailorable platform for biologically interfacing materials, including electrodes and drug delivery. Non-porous nanoparticle doped polymers demonstrate outstanding stability under electrical stimulations. Incorporation of one or more pharmaceutical agents into porous particles enables a highly efficacious drug delivery platform, increasing yield and enabling delivery of cationic and even electroactive compounds.

In some embodiments, a coated electrode comprising a coating of a conductive polymer doped with negatively charged silica nanoparticles on a conductive surface of the electrode is provided. The conductive polymer can be, for example, poly 3,4 ethylene dioxythiophene (PEDOT). In some embodiments, the negatively charged silica nanoparticles are sulfonated silica nanoparticles. In some embodiments, the coating of the conductive polymer on the electrode is formed by electropolymerization of a mixture of monomers of the conductive polymer and the negatively charged silica nanoparticles onto a conductive surface of the electrode. In some embodiments, the negatively charged silica nanoparticles are mesoporous. In some embodiments, the mesoporous negatively charged silica nanoparticles are loaded with one or more pharmaceutical agents that are electronically triggered to release from the mesoporous nanoparticles into the surrounding environment of the conductive polymer.

Medical implants are also provided. In some embodiments, the medical implant comprises one or more electrodes comprising a coating of the conductive polymer doped with negatively charged silica nanoparticles on a conductive surface.

The conductive polymer and/or the coated electrode are useful, for example, in methods of recording or stimulating a bio-electric signal in a subject or tissue. In examples comprising drug-loaded mesoporous silica nanoparticles, the conductive polymer (or a medical implant comprising the conductive polymer) may be used in a method of administering a pharmaceutical agent to a subject or tissue.

The foregoing and other objects, features, and advantages of the embodiments will become more apparent from the following detailed description, which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 3A) DLS measured diameter and (FIG. 3B) DLS measured Zeta potential of synthesized nanoparticles. (FIG. 3C) and (FIG. 3D) TEM images of mesoporous and non-porous particles, respectively. *$p<0.05$ *$p<0.001$ **$p<0.0001$ FIGS. 4A-4I.

FIGS. 6A-6F. Fluorescein (FIG. 6A) and rhodamine (FIG. 6B) loaded PEDOT/SNP films were compared to their respective drug only analog. (FIG. 6C) Co-release of fluorescein and rhodamine under the same conditions as (FIG. 6A) and (FIG. 6B). (FIGS. 6D-6F) are the total drug loaded into the films of FIGS. 6A-6C, respectively. *$p<0.05$ **$p<0.01$ FIGS. 7A-7D.

FIGS. 8A-8H. (FIG. 8A) Experimental set-up. (FIG. 8B) fluorescence for each pulse compared to baseline. (FIG. 8C) and (FIG. 8D) are representative images of the fluorescence before and during stimulation of fluorescein. (FIG. 8E) quantification of GCaMP activity before and during stimulation through an unloaded electrode. (FIG. 8F) Quantification of GCaMP activity before and during activity of a DNQX loaded electrode. (FIG. 8G) and (FIG. 8H), pixel standard deviations for pre and during stimulation frames for a DNQX loaded electrode, respectively. *$p<0.05$ FIGS. 9A-9C.

FIGS. 10A-10F. (FIG. 10A) XTT assay absorbance, proportional to the viability of cells. (FIG. 10B) The counts of live/dead staining on each substrate. (FIGS. 10C-10F) Live dead stains of PEDOT/SNP, PEDOT/PSS, control cells grown on TCPS, and control cells grown on TCPS but killed prior to testing with 0.2% Triton-X. $p<0.01$ **$p<0.0001$ FIG. 11. Median polymerization potentials for drug loaded films. PEDOT films were polymerized for 200 seconds under constant current, with the voltage at 100 s recorded.

(FIG. 12A) A Pt/Ir wire was coated with PEDOT/SNP which was preloaded with either fluorescein or rhodamine-b. The wire was stimulated with a biphasic linear voltage sweep (CV from −0.6V to 0.8V), resulting in stimulation and delay periods. Representative images from the release are shown in (FIG. 12A) for the pre-release (Stim Off), reducing voltage (Stim On), and oxidizing voltage (Stim Delay). The fluorescence was quantified during the stimulation and delay periods (FIG. 12B).

(FIG. 13A) Fluorescein, (FIG. 13B) Rhodamine, and (FIG. 13C) both dyes were released from PEDOT/SNP films.

DETAILED DESCRIPTION

I. Introduction

Figure 1:
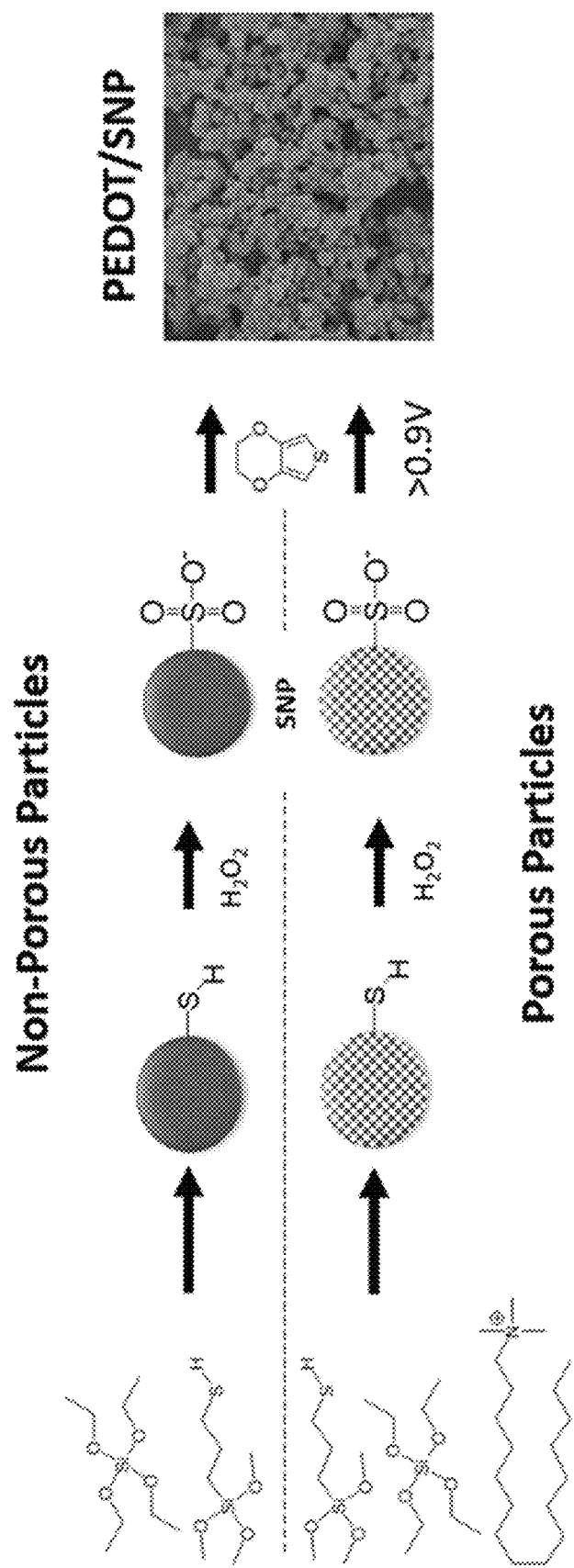
FIG. 1. Particle synthesis and polymerization of PEDOT/SNP. Thiol modified silica nanoparticles are synthesized from tetraethyl orthosilicate and mercaptopropyl trimethoxysilane, with the inclusion of hexadecyl trimethylammonium bromide producing a porous particle structure. The thiol groups are then oxidized to sulfonate under hydrogen peroxide, allowing the particle to serve as a conducting polymer dopant. The particles are then mixed with 3,4-ethylenedioxythiophene (EDOT), and polymerized to form a conducting-polymer/nanoparticle composite for stimulation, recording, and drug delivery.

In order to address certain material limitations of conductive polymers, for example for use with biologically interfacing electrodes, provided herein is a novel conductive polymer with a silica-based nanoparticle dopant. In several embodiments, the nanoparticle dopant is synthesized from silica precursors to form a thiol modified particle, following which the particles are oxidized to display sulfonate functional groups that are used to dope the conductive polymer for electrode coating. Mixture of the sulfonated silica nanoparticles with monomers of the conductive polymer during the coating process (e.g., electrodeposition) allows for formation of the coating on conductive surface of an electrode.

Dopants have a large impact on the properties of conducting polymer films. Many dopants for conductive polymers are small molecules and ions, such as chlorine, perchlorate, and toluene-sulfonate. Polymeric and two- and three-dimensional dopants have also demonstrated to excellent conducting polymer films, with polystyrenesulfonate, graphene and graphene oxide, metal nanoparticles, and carbon nanotubes all being investigated as dopants for conducting polymer films. Interestingly, the large dopants investigated have been highly conductive, with prevailing wisdom in the field dictating that large non-conductive nanoparticles will interfere with the electrochemical properties of the doped polymer.

Silica itself is highly insulating; accordingly, the conductive polymer provided herein has properties contradicting the expectations of the field. As shown herein, the doped conductive polymer is highly conductive, allowing for efficient charge transfer. Surprisingly, the conductive polymer maintains and exceeds the charge injection abilities of similar polymer lacking the silica nanoparticle dopants.

Further, selective inclusion of a surfactant, such as hexadecyl trimethylammonium bromide (CTAB) with the silica precursors during nanoparticle generation allows for synthesis of porous silica-based nanoparticles, which can be loaded with one or more pharmaceutical agents. Release of the agent from the nanoparticle is electrically triggered.

The conductive polymer doped with non-porous nanoparticles possesses low interfacial impedance, high charge injection (4.8 mC cm$^{-2}$), and excellent stability under repetitive stimulation, desired features for improving electrical recording and stimulation performance of neural electrodes. Meanwhile, porous silica nanoparticle dopants can serve as drug reservoir and greatly enhanced the capability of conducting polymer based, electrically controlled drug release technology. Using the silica nanoparticle dopants, the drug load and release was increased up to 16×, and the range of releasable drugs is expanded to include both cationic and electroactive compounds, while maintaining their bioactivity.

II. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the term "comprises" means "includes." It is further to be understood that all molecular weight or molecular mass values are provided for descriptive purposes, unless otherwise indicated. Although many methods and materials similar or equivalent to those described herein can be used, particular suitable methods and materials are described below. In addition, the materials, methods, and examples are illustrative only and not intended to be limiting. The scope of the claims should not be limited to those features exemplified. To facilitate review of the various embodiments, the following explanations of terms are provided:

About: Unless context indicated otherwise, "about" refers to plus or minus 5% of a reference value. For example, "about" 100 refers to 95 to 105.

Administration: To provide or give to a subject a pharmaceutical agent by any effective route.

Antioxidant: A substance that, when present in a mixture or structure containing an oxidizable substrate molecule (for example, an oxidizable biological molecule), significantly delays or prevents oxidation of the oxidizable substrate molecule. Antioxidants can act by scavenging biologically important reactive free radicals or other reactive oxygen species (ROS), or by preventing their formation, or by catalytically converting the free radical or other ROS to a less reactive species. Cells have endogenous antioxidant machinery, such as superoxide dismutase.

Bioelectrical signal: An electrical signal originating in tissue or cells from or in a subject. "Recording a bioelectrical signal" refers to recording an electrical signal that independently exists outside of the membrane or wall of a cell. "Stimulating a bioelectrical signal" refers to application of an electrical current to tissue or cells in such a way as to cause the tissue or cells to produce an electrical signal (e.g., an action potential). An extracellular electrical signal can, however, originate in a cell. An extracellular electrical signal is contrasted with an intracellular electrical signal, which originates, and remains, in a cell. An extracellular electrical signal can comprise a collection of extracellular electrical signals generated by one or more cells. In some embodiments, the bioelectrical signal is a neural signal, which is an electrical signal originating in the nervous system or tissue of a subject.

Coated electrode: An electrode with a layer of material that partially or fully covers the conductive surface (or surfaces) of the electrode. The layer of material is itself conductive. For example, a conductive polymer can be electrodeposited on the conductive surface of an electrode to generate an electrode coated with the conductive polymer. The conductive surface of the electrode does not need to be completely coated (and in many cases is partially coated). Further, the amount of coating can vary according to the application parameters, e.g., time of use, exposure, level of signals, levels of noise, desired compound density, etc. The coat or coating on a coated electrode is the layer of material that partially or fully covers the conductive surface (or surfaces) of the electrode.

Conductive polymer: An organic molecule of repeating structural units (monomers) that conducts electricity. In several embodiments, the conductive polymers provided herein can be formed by electrodeposition on an electrode. Non-limiting examples of conductive polymers for use in the embodiments disclosed herein include poly 3,4 ethylene dioxythiophene (PEDOT), poly pyrrole (PPy) and its derivatives, polythiophene and its derivatives, and polyaniline.

Doping and Dopants: Doping is the process of oxidizing (p-doping) or reducing (n-doping) a neutral polymer and providing a counter anion or cation (the dopant). Doping can also occur during electropolymerization process, in which monomers are oxidized and polymerized into charged long chain molecules while counter ions nearby incorporated via electrostatic force. Upon doping, a conductive polymer system with a net charge of zero is produced due to the close association of the counterions with the charged conductive polymer backbone. In some examples, dopants can catalyze the polymerization of monomers during synthesis. The disclosed embodiments include negatively charged silica nanoparticles as dopants in a conductive polymer, which alter the conductive properties of the polymer. The negatively charged silica nanoparticles interact with the positive charge of the conductive polymer backbone. A "doped" conductive polymer is a conductive polymer including a dopant.

Effective amount: The "effective amount" of a composition or agent is the quantity of the composition or agent sufficient to achieve a desired result.

Electrode: An electric conductor through which an electric current can pass. An electrode can also be a collector and/or emitter of an electric current. In some embodiments, an electrode is a solid and comprises a conducting metal as the conductive layer. Non-limiting examples of conducting metals include noble metals and alloys, such as stainless steel and tungsten.

Implanting: Completely or partially placing a medical device within a subject, for example, using surgical techniques. A device is partially implanted when some of the device reaches, or extends to the outside of, a subject. Implantable devices may be implanted into neural tissue, such as the central nervous system, more particularly the brain, for treatment of different medical conditions and for various time periods. A neural device can be implanted for varying durations, such as for a short term duration (e.g., one or two days or less) or for long-term or chronic duration (e.g., one month or more).

Medical Implant: Any device intended to be partially or wholly introduced, inserted, or implanted within a subject's body for one or more therapeutic or prophylactic purposes, such as for restoring physiological function, alleviating symptoms associated with disease, delivering therapeutic agents, detecting changes (or levels) in the internal environment, and/or repairing or replacing or augmenting damaged or diseased organs and tissues.

Non-limiting examples of medical implants include cardiac pacemaker, a cardiac defibrillator, a deep brain stimulator, a cochlear implant, a peripheral nerve stimulator, a spinal cord stimulator, a neural electrode, an enteric nervous system stimulator, a skin surface electrode (such as ECG, EMG and EEG electrode), an intramuscular electrode, or an implantable glucose sensor.

In some embodiments, the medical implant can be a neural implant, which can be any medical implant including one or more electrodes that can be placed in contact with neuronal tissue in an animal host and can record and/or stimulate neural signals from or to the neuronal tissue. Neural probes typically include conductive and non-conductive surfaces designed for contact with neuronal tissue when implanted in a subject, and can include one or more electrodes that can be independently monitored from other conductive surfaces on or off the probe) for recording and/or stimulating neural signals. In several embodiments, the disclosed probes are included in a device (such as an array or a deep brain stimulator) for recording and/or stimulating a neural signal in a subject.

Negatively charged silica nanoparticle: A solid silica-based colloidal particle that has a negative charge and that has an average diameter of from about 10 to about 500 nm. In several embodiments, the negative charge of the silica nanoparticle is due to functionalization with sulfonate groups during the manufacture of the particle. A mesoporous negatively charged silica nanoparticle is one with pores having an average diameter of from about 1 to about 20 nm. The pores can be formed, for example, by including a surfactant (such as hexadecyl trimethylammonium bromide, CTAB) in the solution of silica precursors used to make the nanoparticle. The average diameter of the pores is typically no more than 10% of the average diameter of the negatively charged silica nanoparticle. A mesoporous negatively charged silica nanoparticle that is loaded with a pharmaceutical agent has the pharmaceutical agent in the pores of the nanoparticle and release of the agent from the nanoparticle is electrically triggered by applying upon application of a potential.

Pharmaceutical agent: A chemical compound or composition capable of inducing a desired therapeutic or prophylactic effect when properly administered to a subject or a cell.

Small molecule: A molecule, typically with a molecular weight less than 1000, or in some embodiments, less than about 500 Daltons, wherein the molecule is capable of inhibiting or activating, to some measurable extent, an activity of some target molecule.

Subject: Living multi-cellular vertebrate organisms, a category that includes human and non-human mammals, including non-human primates, rats, mice, guinea pigs, cats, dogs, cows, horses, and the like. Thus, the term "subject" includes both human and veterinary subjects.

III. Conductive Polymers, Coated Electrodes, and their Use

Provided herein are embodiments of a conductive polymer doped with negatively charged silica nanoparticles. Further provided are embodiments of a coated electrode comprising a coating of the conductive polymer doped with negatively charged silica nanoparticles on a conductive surface of the electrode.

The electrode can be made of any suitable material that allows for the coating with the conductive polymer doped with the negatively charged silica nanoparticles. For example, in some embodiments, the electrode is a gold electrode, a platinum electrode, an iridium electrode, a glassy carbon electrode, a steel electrode, a tungsten electrode, a magnesium electrode, or a carbon fiber electrode. In several embodiments, the electrode is suitable to record or stimulate a bioelectric signal at the target location in tissue of a subject.

The conductive polymer of the coating can be any suitable conductive polymer that can be electrodeposited on a conductive surface of the electrode. In some embodiments, the conductive polymer is poly 3,4 ethylene dioxythiophene (PEDOT).

Conductive polymers (such as PEDOT) can be controllably deposited on a substrate surface via the application of a potential sufficient to oxidize and polymerize monomer of the conductive polymer. The introduction of a thin conductive polymer film increases the effective surface area in addition to incorporating a specific reactive surface on the electrode substrate without sacrificing the conductive property of the electrode. Poly(3,4-ethylene dioxythiophene) (PEDOT) can be electro-polymerized from 3,4-ethylene dioxythiophene (EDOT) monomers. The oxidative polymerization of PEDOT results in positive charges on the polymer backbone, which allows for the incorporation of negatively charged doping agents, such as silica nanoparticles modified to have a negative charge, such as sulfonated silica nanoparticles.

Accordingly, the coating of the conductive polymer on the coated electrode is typically formed by electrodeposition of monomers of the polymer on a conductive surface of the electrode, although any suitable means may be used to coat the conductive surface of the electrode with the conductive polymer. In several embodiments, the coating is formed by electropolymerization of a mixture of monomers of the conductive polymer and the negatively charged silica nanoparticles onto a conductive surface of the electrode. In some embodiments, the conductive polymer is PEDOT, and the coating is formed by electropolymerization of a mixture of 3,4 ethylene dioxythiophene (EDOT) monomers and the negatively charged silica nanoparticles onto the conductive surface of the electrode.

Any suitable amount of conductive polymer may be coated on the conductive surface of the coated electrode. In some embodiments, the coating on the electrode is from about 25 $mC\ cm^{-2}$ to about 2 $C\ cm^{-2}$ as measured during electrodeposition, such as from about 25 $mC\ cm^{-2}$ to about 2 $C\ cm^{-2}$, from about 25 $mC\ cm^{-2}$ to about 1 $C\ cm^{-2}$, from about 25 $mC\ cm^{-2}$ to about 750 $mC\ cm^{-2}$, from about 25 $mC\ cm^{-2}$ to about 500 $mC\ cm^{-2}$, from about 50 $mC\ cm^{-2}$ to about 500 $mC\ cm^{-2}$, from about 100 $mC\ cm^{-2}$ to about 500 $mC\ cm^{-2}$, from about 2 $mC\ cm^{-2}$ to about 250 $mC\ cm^{-2}$, from about 50 $mC\ cm^{-2}$ to about 250 $mC\ cm^{-2}$, from about 100 $mC\ cm^{-2}$ to about 250 $mC\ cm^{-2}$, from about 25 $mC\ cm^{-2}$ to about 100 $mC\ cm^{-2}$, or from about 25 $mC\ cm^{-2}$ to about 50 $mC\ cm^{-2}$, as measured during electrodeposition.

The conductive polymer is doped with negatively charged silica nanoparticles. Any suitable negatively charged silica nanoparticle can be used as a dopant in the conductive polymer. In some embodiments, the negatively charged silica nanoparticles are sulfonated silica nanoparticles. The negatively charged silica nanoparticles can be any suitable size. In some embodiments, the negatively charged silica nanoparticles have an average size of from about 10 to about 500 nm in diameter, such as from about 10 to about 100 nm in diameter, from about 50 to about 500 nm in diameter, from about 100 to about 500 nm in diameter, from about 200 to about 500 nm in diameter, from about 10 to about 250 nm in diameter, from about 100 to about 250 nm in diameter, or from about 50 to about 250 nm in diameter.

The coating on the electrode is more stable due to the negatively charged silica nanoparticle dopant. For instance, as shown in the examples, the impedance and charge storage capacity of the electrode coated with the conductive polymer doped with negatively charged silica nanoparticles remain stable following sonication for 60 minutes, whereas a control conductive polymer with a different dopant is not stable.

In some embodiments, the conductive polymer is doped with solid negatively charged silica nanoparticles, that is, nanoparticles that are not porous.

In some embodiments, the conducive polymer is doped with negatively charged silica nanoparticles that are mesoporous. For example, the mesoporous negatively charged silica nanoparticles may comprise pores having an average diameter of from about 1 nm to about 20 nm, such as from about 2 nm to about 20 nm, from about 5 nm to about 20 nm, from about 10 nm to about 20 nm, from about 1 nm to about 10 nm, from about 1 nm to about 5 nm, from about 2 nm to about 5 nm, from about 2 nm to about 10 nm, or from about 5 nm to about 15 nm.

The mesoporous negatively charged silica nanoparticles may be generated using any suitable method. In some embodiments, the mesoporous negatively charged silica nanoparticles are generated by a process comprising incubating a mixture of silica precursors and a surfactant under conditions sufficient to form negatively charged silica nanoparticles. The surfactant forms a micelle in the mixture and can be removed following nanoparticle formation, leaving pores in the nanoparticle. Non-limiting examples of surfactants that can be used in the generation of mesoporous negatively charged silica nanoparticles include hexadecyl trimethylammonium bromide (CTAB), hexadecyl trimethylammonium chloride (CTACL), Triton-X, and poly(ethylene-oxide) derivatives. By varying the type of surfactant, or combination thereof, the pore size and organization can be tailored as needed.

In some embodiments, the conducive polymer is doped with mesoporous negatively charged silica nanoparticles that are loaded with a pharmaceutical agent. Any suitable pharmaceutical agent can be loaded on the mesoporous negatively charged nanoparticles as long as the agent is retained in the pores of the nanoparticle under physiological conditions, and released from the nanoparticle upon application of an appropriate potential to the conductive polymer. Loading of the pharmaceutical agent on to the mesoporous nanoparticles can be accomplished by any suitable technique, a non-limiting example is incubating the negatively charged mesoporous silica nanoparticles with the small molecules drug in a solution, and sonicating the solution to load the small molecules drug on to the negatively charged mesoporous silica nanoparticles. In some embodiments, the pharmaceutical agent is a small molecule drug. In some embodiments, the pharmaceutical agent is an anti-oxidant, an anti-inflammatory agent, an anti-convulsant agent, an anti-bacterial agent, or an anti-cancer agent. Non-limiting examples of pharmaceutical agents that can be loaded on to the negatively charged silica nanoparticles include melatonin, dexamethasone, minocycline, glutamate, gamma aminobutyric acid (GABA), dopamine, muscimol, bicuculline, AP-5(amino-5-phosphonovaleric acid), 6,7-dinitroquinoxaline-2,3-dione (DNQX), 6-cyano-7-nitroquinoxaline-2,3-dione, and doxorubicin.

As used herein, a mesoporous negatively charged silica nanoparticle "loaded" with a pharmaceutical agent contains the pharmaceutical agent in the pores of the nanoparticle, where the agent is retained under physiological conditions. Application of an electrical potential to the conductive polymer triggers release of the pharmaceutical agent from the pores of the nanoparticles into the surrounding environment. Non-limiting examples of suitable types of electrical potential to trigger release of the pharmaceutical agent include cyclic voltammetric, sinusoidal, cosine wave, and square wave electrical stimulus.

The drug-loaded conductive polymer can be used in methods of administering a pharmaceutical agent loaded onto the nanoparticles to a subject or tissue in which the conductive polymer is implanted. In some embodiments, a method is provided comprising implanting a medical implant at a target location in a subject (or in tissue from a subject), wherein the implant comprises one or more electrodes coated with the conductive polymer doped with mesoporous silica nanoparticles loaded with a pharmaceutical agent as described herein. Following implantation, a potential is applied across the one or more electrodes to release the pharmaceutical agent from the mesoporous negatively charged silica nanoparticles in the coating to the surrounding environment of the tissue or subject.

In some embodiments, a method of making an electrode comprising a coating of a conductive polymer doped with negatively charged silica nanoparticles on a conductive surface of the electrode is provided. The method comprises incubating a mixture of monomers of a conductive polymer and negatively charged silica nanoparticles with a conductive surface of an electrode, and applying a potential sufficient to oxidize and polymerize the monomers on the conductive surface of the electrode to form a coating of the conductive polymer doped with the negatively charged silica nanoparticles at the conductive surface of the electrode. In several embodiments, the monomers of the conductive polymer are 3,4 ethylene dioxythiophene (EDOT) monomers and the method forms a coated electrode comprising a coating of poly-3,4 ethylene dioxythiophene (PEDOT) doped with negatively charged silica nanoparticles.

In some embodiments, the method further comprising making the negatively charged silica nanoparticles. In such embodiments, the method further comprises incubating silica precursors comprising one or more thiol groups under conditions sufficient to form silica nanoparticles, thereby forming thiol modified silica nanoparticles. The thiol functional groups of the thiol modified silica nanoparticles are oxidized to form sulfonated silica nanoparticles. The sulfonate groups on the sulfonated silica nanoparticles carry a negative charge, which forms the negatively charged silica nanoparticles. In some embodiments, the negatively charged silica nanoparticles produced with the disclosed method are mesoporous. In such embodiments, a surfactant (such as CTAB) is included with the silica precursors comprising one or more thiol groups when they are incubated under conditions sufficient to form silica nanoparticles. The surfactant forms micelles and can be removed following nanoparticle formation, leaving pores in the nanoparticle.

In some embodiments, the conductive polymer doped with negatively charges silica nanoparticles is removed from the electrode surface following electrodeposition. This provides a conductive polymer doped with negatively charged silica nanoparticles. The conductive polymer can be used for any application that would benefit from such a polymer, for example, transdermal drug delivery and controlled drug delivery after implantation.

IV. Medical Implants

In several embodiments, a medical implant is provided that includes one or more electrodes coated with the conductive polymer doped with negatively charged silica nanoparticles as described herein. In several embodiments, the medical implant includes one or more electrodes coated with a drug-loaded conducted polymer as described herein; such an implant can be used, for example, to administer the drug to a target location in a subject.

In some embodiments, the medical implant is designed for full or partial implantation into a subject or tissue from a subject, such as any mammal, including humans, non-human primates, pigs, sheep, cows, rodents and the like.

The medical implant can be any type of medical implant that would benefit from having one or more electrodes coated with the conductive polymer doped with negatively charged silica nanoparticles (such as drug-loaded mesoporous negatively charged silica nanoparticles) as described herein. For example, in some embodiments, the medical implant is a cardiac pacemaker, a cardiac defibrillator, a deep brain stimulator, a cochlear implant, a peripheral nerve stimulator, a spinal cord stimulator, a neural electrode, an enteric nervous system stimulator, a skin surface electrode (such as ECG, EMG and EEG electrode), an intramuscular electrode, or an implantable glucose sensor.

In some embodiments, the medical implant is a neural implant comprising one or more electrodes coated with the conductive polymer doped with the negatively charged silica nanoparticles.

Numerous types and styles of neural implants including one or more electrodes for recording and/or stimulating a neural signal are available, and known to the person of ordinary skill in the art. Any neural implant for recording and/or stimulating neural signals in a subject may be used with the disclosed embodiments. In several embodiments, the neural implant includes more than one electrode, such as an array of electrodes. In additional embodiments, a device is provided that can include one or more neural probes, each of which can include one or more electrodes. Non-limiting examples include deep brain stimulators, EcoG grids, electrode arrays, microarrays (e.g., Utah and Michigan microarrays), and microwire electrodes and arrays.

In several embodiments, a disclosed medical implant can be used for recording and/or stimulating bio-electric (e.g., neural) signals in a subject. For example, the medical implant can be implanted into neuronal tissue of the subject, and used to record and/or stimulate neural signals from the subject for a period of at least 1 month (such as at least 2, 6, 12, 18, 24, 30 or 36 or more months).

In some embodiments, the neural implant is typically linked to circuitry for recording and/or stimulating a neural signal via the one or more electrodes included on the implant. In some embodiments, the integrated circuits can be fully implanted (typically implantable in a subcutaneous pocket within a patient's body) or partially implanted in the patient, but are not limited thereto. The operable linkage to the neural implant or device can be by way of one or more leads, although any operable linkage capable of transmitting the measured neural signal from the electrodes to the circuitry, or a stimulation signal from the circuitry to the electrodes, can be used.

In some embodiments, the integrated circuitry includes a stimulator linked to the device and suitably designed for application of various current, voltage, pulse rate, waveforms etc., for generating a neural signal in one or more neurons in proximity to the electrode or electrodes included on the device. For example, the stimulator can be separate from the integrated circuitry or it can be included in the same housing as the integrated circuitry.

EXAMPLES

The following examples are provided to illustrate particular features of certain embodiments, but the scope of the claims should not be limited to those features exemplified.

Example 1

Nanoparticle Doped PEDOT for Enhanced Electrode Coatings and Drug Delivery

In order to address the material limitations of biologically interfacing electrodes, modified silica nanoparticles are utilized as dopants for conducting polymers. Silica precursors are selected to form a thiol modified particle (TNP), following which the particles are oxidized to display sulfonate functional groups (SNP). The selective inclusion of hexadecyl trimethylammonium bromide (CTAB) allows for synthesis of both porous and non-porous SNPs. Non-porous nanoparticle doped polyethylenedioxythiophene (PEDOT) films possess low interfacial impedance, high charge injection (4.8 mC cm$^{-2}$), and excellent stability under repetitive stimulation. Porous SNP dopants can serve as drug reservoirs and greatly enhanced the capability of conducting polymer based, electrically controlled drug release technology. Using the SNP dopants, drug loading and release is increased up to 16.8×, in addition to greatly expanding the range of drug candidates to include both cationic and electroactive compounds, all while maintaining their bioactivity. Finally, the PEDOT/SNP composite is capable of precisely modulating neural activity in vivo by timed release of a glutamate receptor antagonist from coated microelectrode sites. Together, this work demonstrates the feasibility and potential of doping conducting polymers with engineered nanoparticles, which creates countless options to produce composite materials for enhanced electrical stimulation, neural recording, chemical sensing, and on demand drug delivery.

1. Introduction

Conducting polymers have gained substantial attention in recent years as an advanced coating for microelectrodes,[7] with particular emphasis on the polypyrrole[8-10] and poly 3,4-ethylene dioxythiopene[9, 11-15] (PEDOT). Conducting polymer coatings can be applied to an electrode by immersing the electrode site in a solution of monomer alongside a negatively charge dopant. A positive potential applied to the electrode results in spontaneous oxidation and polymerization of the monomer into a polymer film. These oxidized conducting polymer films possess positive charges along the backbone, which is then balanced out by the anionic dopants. Further polymerization leads to thicker coating with a unique fractal pattern,[12] increasing surface area by orders of magnitude and resulting in dramatically reduced impedances of the electrode.[10, 12] In neural engineering, these coatings are notable for improving recordings from electrodes as small as 7 μm in diameter,[15] lowering thermal noise and increasing the signal to noise ratio of recorded neural action potentials.[14] Similarly, conducting polymer coatings can greatly increase amount of charge which can be injected into tissues prior to the buildup of unsafe potentials.[16-19] These exceptional electrochemical properties have led conducting polymers to be at the forefront of microelectrode design.

Doping offers endless possibilities for tuning the properties of conducting polymer as the dopants carry in their unique characteristics and functionality. Various dopants have been incorporated into conducting polymer from non-bioactive ions,[20, 21] to peptides,[22] proteins,[23-25] polysaccharides,[26] and even cells.[27] Large biomolecules are immobilized this way to impart bioactivity to the conducting polymers,[28] while smaller dopants can be released via ion exchange or electrochemical controls.[3] The electrochemically driven release provides a mechanism for on demand drug delivery systems with precise temporal and spatial control. In such a system, conducting polymers serve as a vehicle for drug delivery, with their oxidized state carrying positively charged matrix serving as a gating mechanism. Applying a sufficient negative potential removes this gating and enables release of the dopant. The result is a highly controlled release mechanism, which is entirely localized only to the site of implantation. Researchers have used conducting polymer-based drug delivery to release therapeutics,[29-32] dyes,[9, 33] and neurotransmitters and neuromodulators.[34, 35]

The primary limitations of conducting polymer-based drug delivery are the quantity of the drug load and the compatibility of pharmacologic compounds. To address the limitation on drug load, drug reservoirs have been incorporated into the polymer film. Examples including nanotubes[32] and nanopores,[33] graphene oxide,[29,30] and functionalized carbon nanotubes[9] (CNT) have been successful in increasing the quantity of the drug payload. The ion pump approach can further circumvent this issue by incorporating a fluid channel and an external reservoir that can be refilled,[34] but this requires extensive microfabrication and is not immediately compatible with many current electrically interfacing devices. When considering candidate drugs suitable for such drug delivery system, anionic compounds are more commonly utilized, as they can directly dope the polymer during polymerization and be released upon de-doping. Loading of neutral and cationic compounds is less straightforward and relies on physical entrapment or interactions with the dopants.[3] Additionally, loaded compound needs to be electrochemically stable under the potentials required for polymerization or for triggering drug release. Until the disclosure provided herein, no viable options to load electroactive compounds have been presented.

This example describes sulfonated silica nanoparticles as dopants for conducting polymers. The silica nanoparticle dopants provide a potential drug delivery reservoir while also maintaining the advantageous electrochemical properties of PEDOT films. The size, porosity and surface chemistry of silica nanoparticles are modifiable,[36, 37] and can be tuned to specific applications. Incorporation of thiol containing silane mercaptopropyl trimethoxysilane (MTS) results in the presentation of thiol groups at the particle surface.[38] These thiol groups can be efficiently oxidized to sulfonates under relatively mild hydrogen peroxide oxidation.[39] The presence of negatively charged sulfonate groups allow the nanoparticles to be effectively doped in the PEDOT matrix. Further, in some embodiments, mesoporous silica is used as the dopant. The highly porous structure of the mesoporous silica nanoparticles enables a large degree of drug loading, while the non-reactive nature of silica renders them biologically inert. Further, the silica nanoparticle dopants are substantially larger than either CNT or graphene, potentially making them capable of more substantial drug loading. Finally, silica itself is non-conductive, shielding the payload from the strong potentials during film polymerization or release triggers.

In this work, we first synthesize sulfonate modified silica nanoparticles (SNPs) with and without mesopores (FIG. 1). We then present SNP-doped PEDOT composites, a biocompatible polymer with highly favorable electrochemical properties. Impedance of gold electrodes was dramatically reduced after coating with PEDOT/SNP, and charge injection limits exceed 4 mC cm$^{-2}$. The mesoporous SNP can carry 16.8 times greater drug load into the polymer film and the drug can be controllably released by cyclic voltage sweeps for over 13000 stimulations. The PEDOT/SNP can load and release not only negative but also positive drugs. More importantly, the electroactive compound melatonin, that would otherwise be oxidized and lose antioxidant efficacy during the electropolymerization process, can be protected by the SNPs. Finally, we utilize our PEDOT/SNP coating to directly modulate neural activity by focal release of neurochemicals, demonstrating the proof of concept for in vivo applications.

2. Results and Discussion 2.1 Synthesis of Nanoparticle Dopants

Figure 3A:
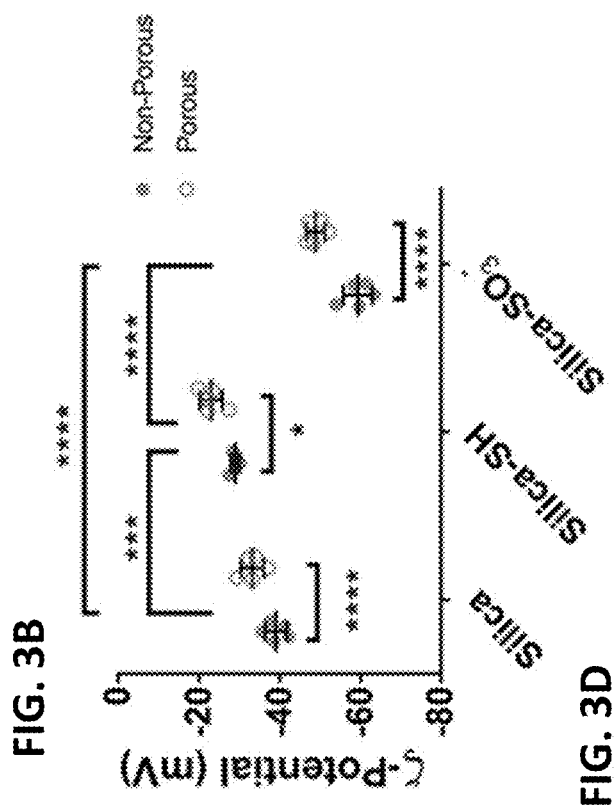
FIGS. 3A-3D.
Figure 3B:
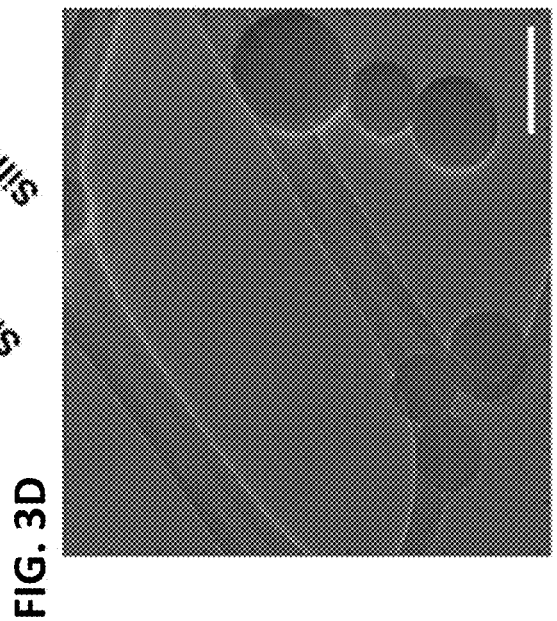
Figure 3C:
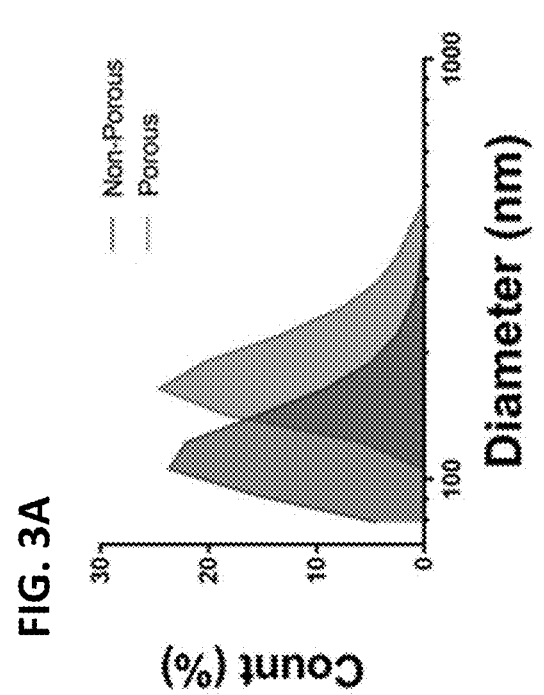
Figure 3D:
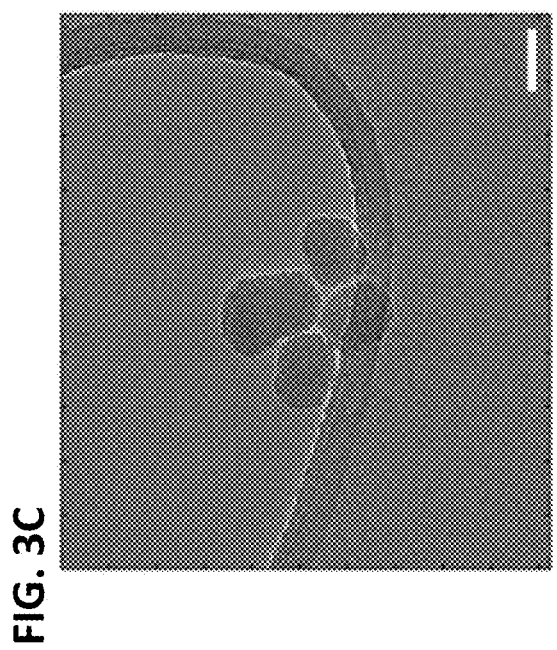

In order to create a nanoparticle capable of doping a conductive polymer film, sulfonate modified silica nanoparticles (SNPs) were developed (FIG. 1). Two distinct SNPs were created and examined for their unique properties, non-porous SNP and mesoporous SNP, which were both synthesized from their respective thiol-modified precursors. Non-porous thiol modified nanoparticles were synthesized from TEOS and MTS under basic conditions. Mesoporous particles were synthesized in the same manner, with the inclusion of CTAB as the surfactant template. After washing, Ellman's reagent was used to verify the presence of thiols, resulting in a distinct color change of the solution from clear to straw yellow. Thiolated nanoparticles (TNP) were subsequently oxidized to SNP under hydrogen peroxide and sulfuric acid. During oxidation, the TNP first aggregate together due to the formation of di-sulfide bonds, but subsequently separate into a homogenous suspension after further oxidation. The resulting SNP did not have an effect when exposed to Ellman's reagent, indicating the absence of the thiol group, which suggests the oxidation to sulfonate. The diameter (FIG. 3A) and zeta potential (FIG. 3B) of the non-porous and mesoporous particles were measured with DLS. SNP possessed significantly greater negative zeta potential than their precursor thiolated particles, further indicating the conversion of the thiol to sulfonate. Similarly, the SNP were more negative than the bare silica, indicating that the SNP possess a permanent negatively charged functional group absent on the bare silica. Non-porous particles had a smaller diameter and more negative zeta potential than the equivalent porous particles. The discrepancy in the zeta potential may be attributed to the difference in the density of the surface functional groups. While the sulfonate groups are expected to be evenly distributed along the surface of both particles, mesoporous particles have a large area removed due to the pores. While the surface area of the porous particles is likely magnitudes larger than the non-porous counterparts, the outer surface charge density is lower, resulting in the seemingly diminished zeta potential. Similar findings and conclusions were drawn by Slowing et al when examining mesoporous and amorphous silica.[41] These particles were further examined under TEM (FIGS. 3C, 3D). The non-porous particles displayed a smooth surface as expected, while the surfactant template left radial pores in the mesoporous particles. These images show a distinct pore structure similar to what was previously reported.[42]

2.2 Electropolymerization and Electrochemical Properties of the PEDOT/SNP

Figure 4C:
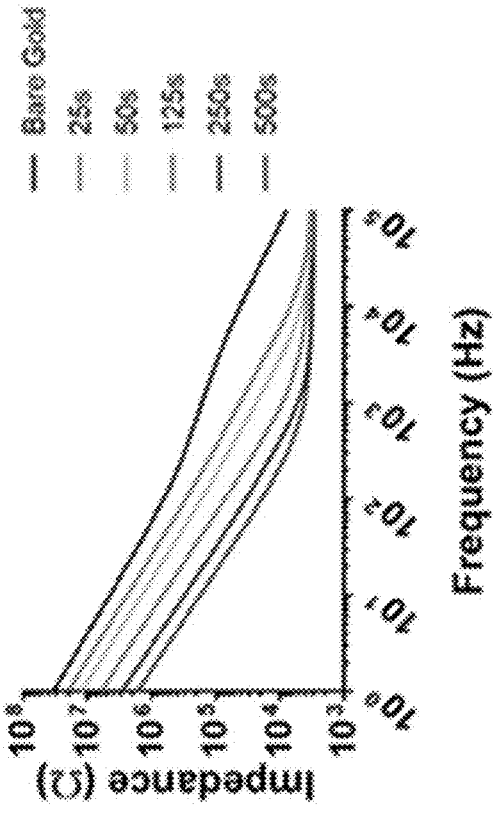
(FIG. 4C) and (FIG. 4E) Impedance and phase (FIG. 4D) and (FIG. 4F) of the electrodes measured in PBS from 1 to 100,000 Hz.
Figure 4D:
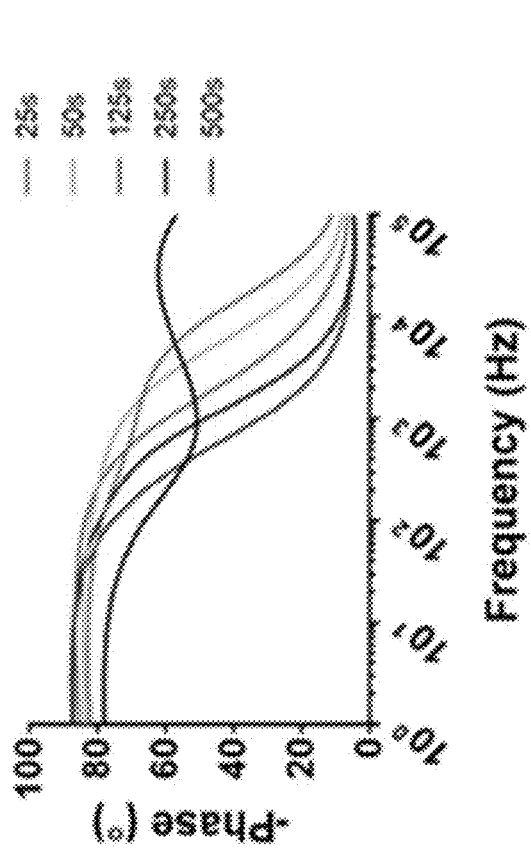
(FIG. 4A) PEDOT/SNP polymer before and after polymerizing on a 2 mm gold electrode.
(FIG. 4B) SEM of PEDOT/SNP surface. The electrochemical properties of PEDOT/SNP polymerized on 50 μm diameter gold electrodes for non-porous (FIGS. 4C, 4D) and porous (FIGS. 4E, 4F) SNP.
(FIG. 4G) and (FIG. 4H) Cyclic voltammetry sweeps of 125 s coated electrodes (green) and bare gold (black) taken at 1 V s$^{-1}$ of non-porous particles and porous particles, respectively.
(FIG. 4I) Charge storage capacity of the films from both solid and porous SNP. *$p<0.05$ FIGS. 5A-5F.
Figure 4A:
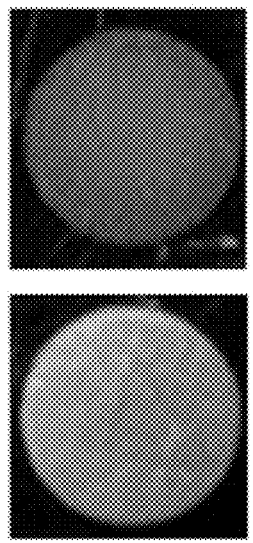
Figure 4B:
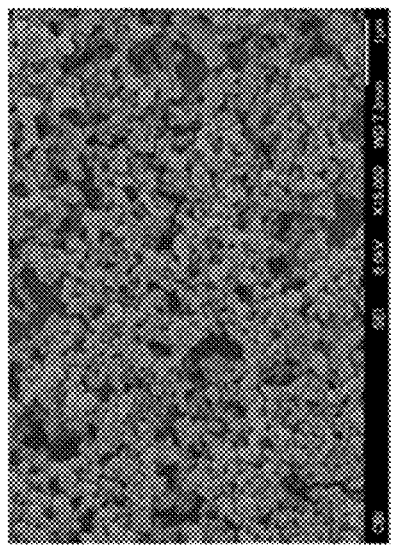

The synthesized SNP were used as a dopant for PEDOT films via electropolymerization. SNPs were suspended in EDOT and electropolymerization was carried out under constant current density of 320 μA cm$^{-2}$. The resulting film was distinctly blue in color, yet notably lighter than films polymerized with common dopants polystyrene-sulfonate or functionalized carbon nanotubes (CNT), most likely due to the translucence of the SNP (FIG. 4A). Examining the structure of the coating under SEM reveals a unique morphology. The particles appear to stack on each other forming a forest-like effect, with individual particles imparting their own geometry to the film (FIG. 4B). Similar observations have been made with very large dopants such as graphene oxide[30] or CNT.[13]

Figure 4E:
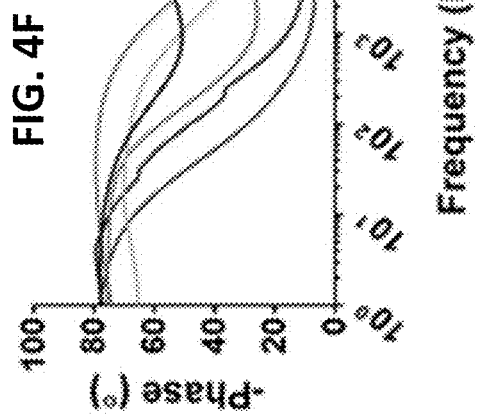
Figure 4F:
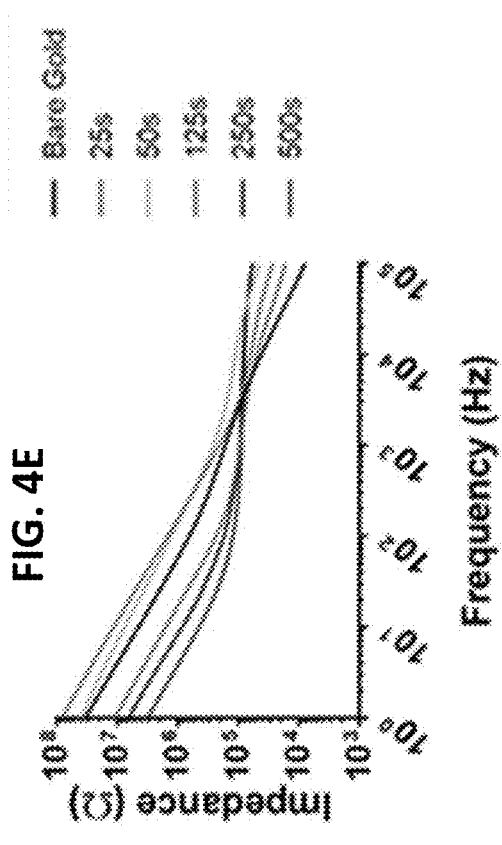
Figure 4I:
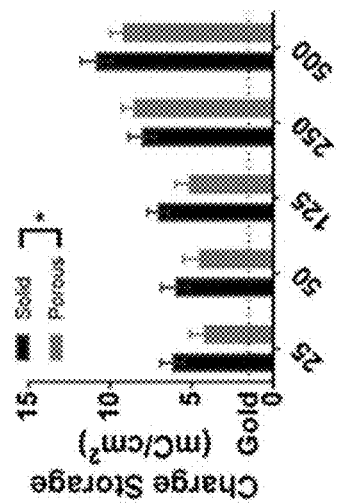
Figure 4H:
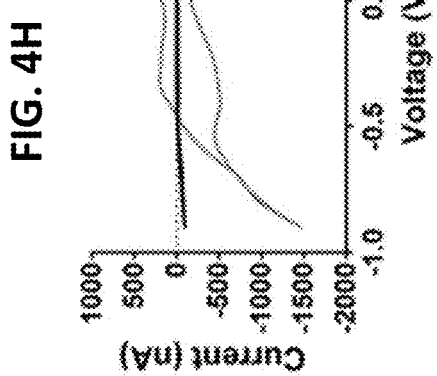
Figure 4G:
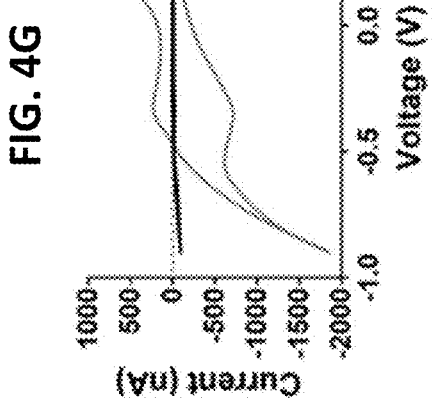

The electrochemical properties of PEDOT/SNP Films were examined utilizing a variety of methods. Directly in line with previous studies concerning conduction polymers, increasing polymerization times of PEDOT/SNP led to decreasing impedance magnitudes (FIGS. 4C, 4E) and leftward-shifts in the cut-off frequency of the EIS (FIGS. 4D,F). The cyclic voltammetry plots demonstrated the characteristic shapes of PEDOT coated electrodes, namely a reduction potential of approximately −0.3V vs Ag/AgCl (FIGS. 4G, 4H). Of note, an interesting difference can be observed between PEDOT/SNP films with solid or porous particles in terms of their respective capacitive and resistive nature. Charge storage capacity (CSC) was derived from the area of the CV plot, which indicates both redox-activity and capacitance of the film. As expected, CSC of the coatings increased with increasing polymerization time as the film grew thicker. Both particles exhibited an increase in CSC with thicker films, although the CSC was significantly higher for solid particles. While both films display dramatically reduced impedances at low frequencies, porous particle films appear to have a higher resistive nature, increasing impedance at higher frequencies above the bare gold electrode. The changes in impedance were likely caused by the decrease in surface charge of the porous particles relative to the solid. However, the porous particle film maintained a high CSC, being only slightly lower than the solid particles and significantly larger than bare gold electrodes (1.5 mC cm$^{-2}$).

Figure 5A:
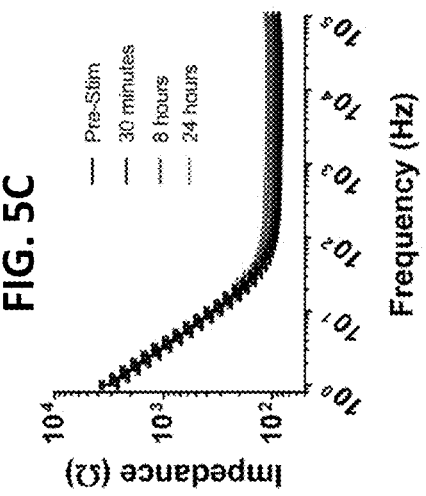
(FIG. 5A) Sample waveform used for charge injection and corresponding voltage transients for gold and PEDOT/SNP. Labeled is the access voltage ($V_a$) and electrode voltage ($V_e$) for the bare gold electrode.
Figure 5B:
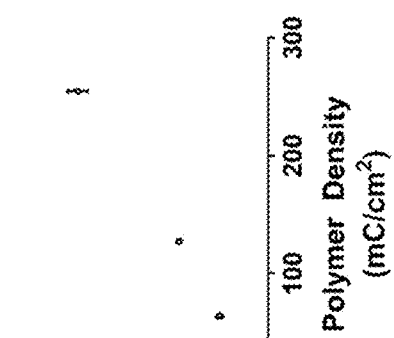
(FIG. 5B) Charge injection calculated for multiple polymer depositions on a 2 mm diameter gold electrode.

Charge injection limit is an important property for electrical stimulation materials. It is defined as the amount of charge that can be passed from the electrode into solution/tissue without causing irreversible electrochemical reactions. Here, charge injection limit was determined by increasing the amplitude of the stimulation current pulses and measuring the voltage transients. Electrode potential was determined by subtracting the access voltage from the peak of the voltage transient, and the current that result in electrode potential of −0.6V was used to deduce the charge injection limit (charge injected per pulse per surface area).[43] Due to their superior electrochemical properties, solid SNP films were used for CIL measurements. A sample current pulse and resulting voltage transient for bare gold and gold coated with PEDOT/SNP are shown (FIG. 5A). Increasing the thickness and amount of deposited polymer resulted in a near linear increase in the CIL (FIG. 5B). CIL of films polymerized for 800 s (a polymer deposition density of 254 mc cm$^{-2}$) have CILs (4.8 mc cm$^{-2}$) in the realm of other advanced coatings such as activated iridium oxide (3.9 mC cm$^{-2}$, 0.4 ms pulse),[43] hydrophilic CNT (1.6 mC cm$^{-2}$, 1 ms pulse),[44] and PEDOT/CNT (2.5 mC cm$^{-2}$, 1 ms pulse).[13]

Figure 5C:
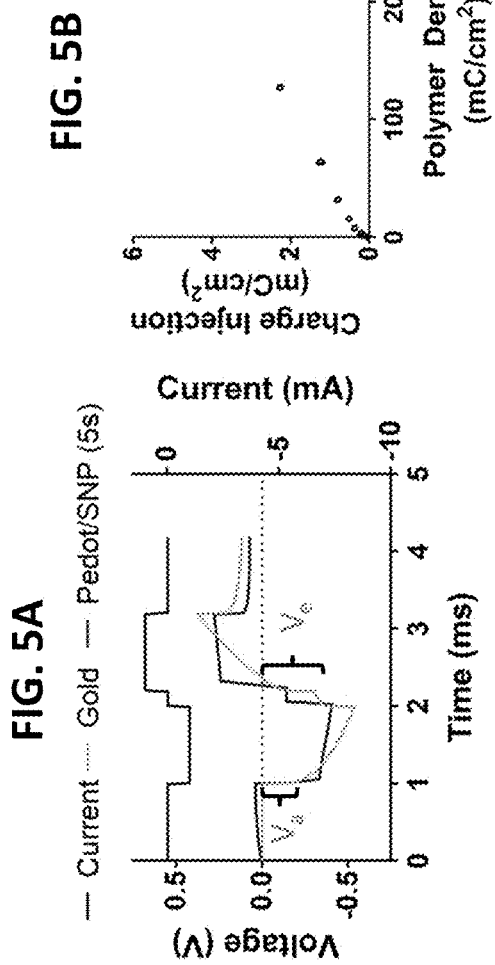
(FIG. 5C) and (FIG. 5D) Impedance and CV measurements taken before chronic stimulation, at 30 minutes, 8 hours, and 24 hours on a 2 mm diameter gold electrode.
Figure 5D:
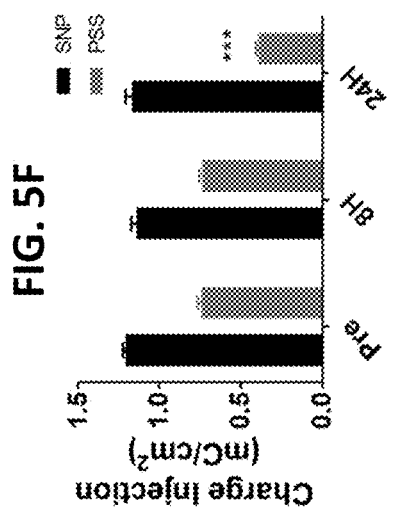
(FIG. 5E) Charge storage capacity (CSC) measured at 0, 30 minutes, 8 hours, and 24 hours for PEDOT/SNP and PEDOT/PSS on a 2 mm gold electrode (FIG. 5F) CSC Charge injection limits for PEDOT/SNP and PEDOT/PSS measured at 0, 8, and 24 hours of chronic stimulation.
Figure 5E:
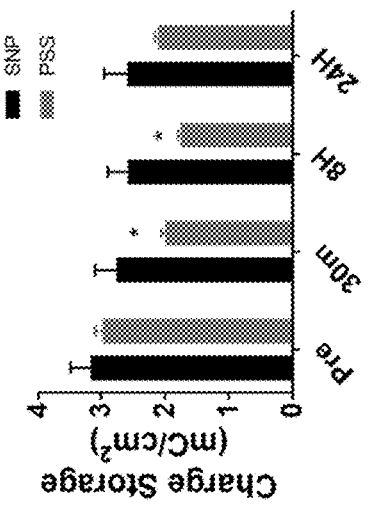
Figure 5F:
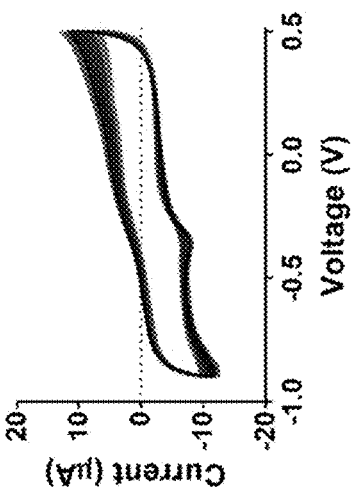
Figures 9A, 9B, 9C:
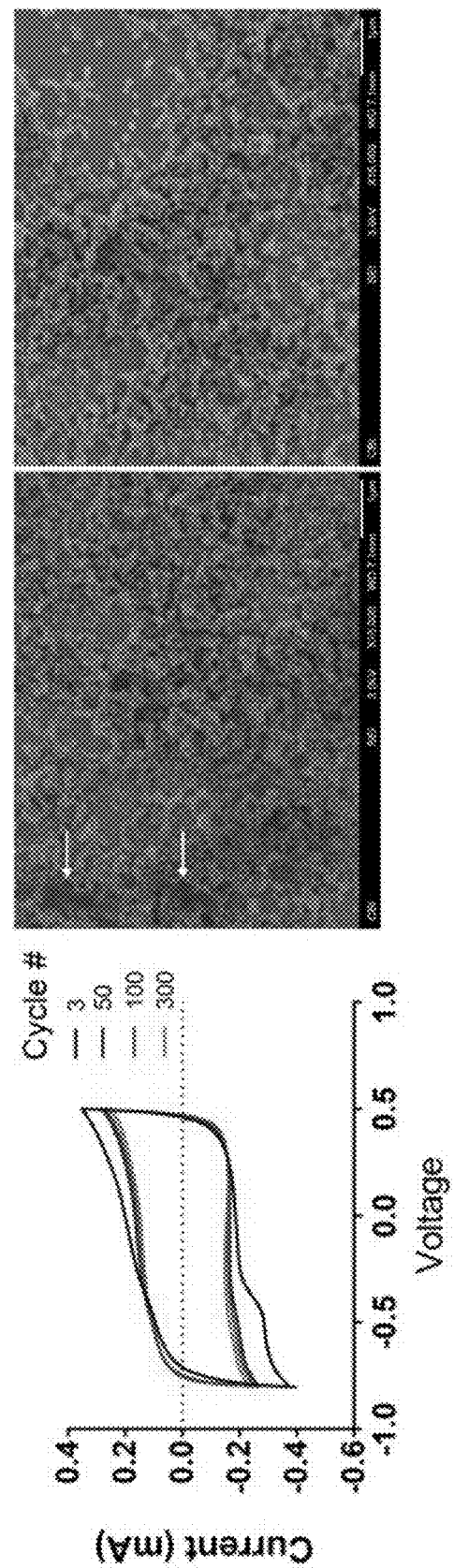
(FIG. 9A) 300 CV cycles of PEDOT/SNP.
(FIG. 9B) Non-sputter coated SEM of the coating before (FIG. 9B) and after (FIG. 9C) stimulation are shown. The morphology of both substrates is dictated predominantly by the nanoparticle dopants, but small differences in the film can be seen. Where the pre-stimulation CV has small clumps of polymer material (white arrows), there is a distinct lack of these features in the post stimulated film.

To test the stability of the coating under stimulation, the coating was subjected to a pulsatile current waveform at 85% of the calculated CIL at 50 Hz for 24 hours (4.32×10$^6$ stimulations). We expect that any changes in electrical properties of the film would be due to either over-oxidation of the PEDOT, leaching of the dopant, or mechanical cracking and delamination of the coating. After stimulation, we did not observe significant changes in the impedance (FIG. 5C), CV scan (FIG. 5D), charge storage capacity (FIG. 5E), or the charge injection limit (FIG. 5F), demonstrating the electrochemical stability of the coating. A similar observation could be made when performing multiple subsequent CV scans on the coating. Following the first scans, the coating had no noticeable change in the CV traces of the 50$^{th}$, 100$^{th}$, or 300$^{th}$ scan (FIG. 9A). Examining the coating before and after subsequent CV scans showed minimal changes in the morphology of the coating (FIGS. 9B, 9C), without any visible cracking or delamination. The electrochemical stability is at least in part due to the size of the dopant particles. Small molecule dopants have a tendency to leach from the conducting polymer matrix,[45] reliably enough to become the basis of conducting polymer based drug release. Large dopants such as SNP are effectively entrapped by the PEDOT network, incapable of diffusing out into solution even when PEDOT undergoes reduction. Additionally, the van der Waals interaction between NPs and substrate may have helped to improve adhesion while the interaction between NPs could also improve the cohesiveness of the coating. Similar observations have been made for other large dopants, such as CNT which improve coating adhesion and stability.[13] Taking the sizable charge injection limits together with the stability of the coating, we show that the PEDOT/SNP polymer is a promising material for chronic stimulation applications.

2.3 Biocompatibility

Figure 12A:
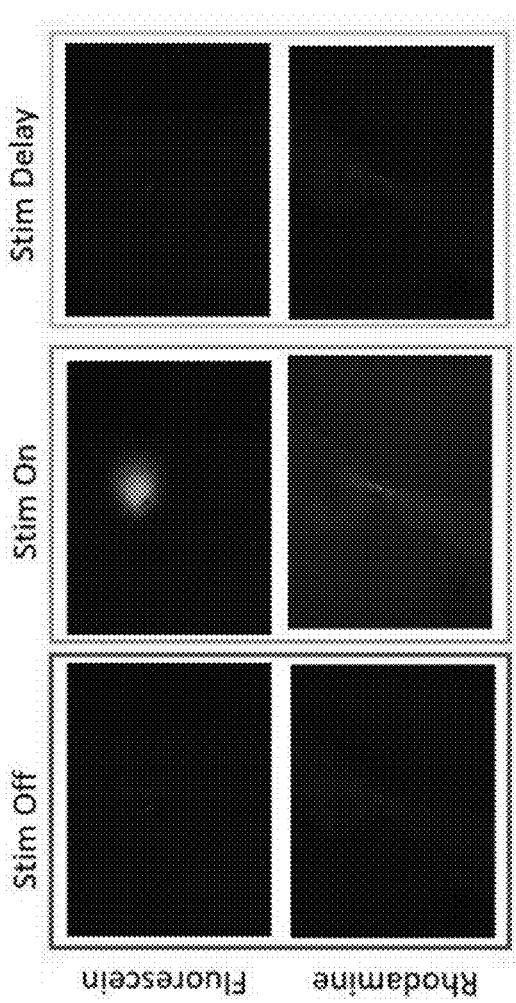
FIGS. 12A and 12B.
Figure 12B:
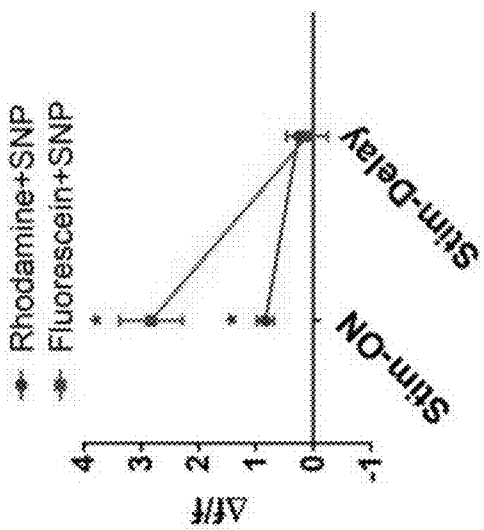

A cytotoxicity assessment was performed on the PEDOT/SNP composite. Both PEDOT[51] and silica nanoparticles[40] have each been successfully employed in in vivo applications. However, small changes to the surface chemistry of the silica nanoparticle warrant investigation into the potential for adverse biological interactions. The commonly employed polymer PEDOT/PSS itself has been previously characterized as non-toxic;[52] and was used as an ideal reference for the toxicity testing of the PEDOT/SNP. The biocompatibility of the PEDOT/SNP surface was evaluated by directly culturing highly aggressive proliferating immortalized (HAPI) microglia cells on the substrate. After 2 days, XTT was used to measure to metabolic activity of the cells. Both PEDOT/PSS and PEDOT/SNP showed significantly lower metabolic activity than control tissue culture polystyrene (86% and 89%, respectively, FIG. 10A), but well within the range of materials considered non-toxic (>80% viability, ISO 10993). Small differences in outgrowth/XTT measurement are likely due to differences in cell adhesion to the substrate, as opposed to interference with metabolic processes or potential toxicity of the substrate. A second set of cultures were stained with Live/Dead staining to visualize the cells on the substrates. A small degree of auto-fluorescence is detectable for both polymer coatings, resulting in a slight amount of red and green background. Live dead staining of the cells on the substrate showed a good distribution and cellular morphology, with minimal dead cells visible. On the other hand, Triton-X treated cells show no viable cells. Quantifying these findings, we again see that no significant differences exist between PEDOT/PSS and PEDOT/SNP (FIG. 12B). Given these findings, we can expect that the PEDOT/SNP surface is safe and non-toxic for acute experimentation, while chronic biocompatibility should still be evaluated.

2.4 Electrically Controlled Drug Release

Figure 2:
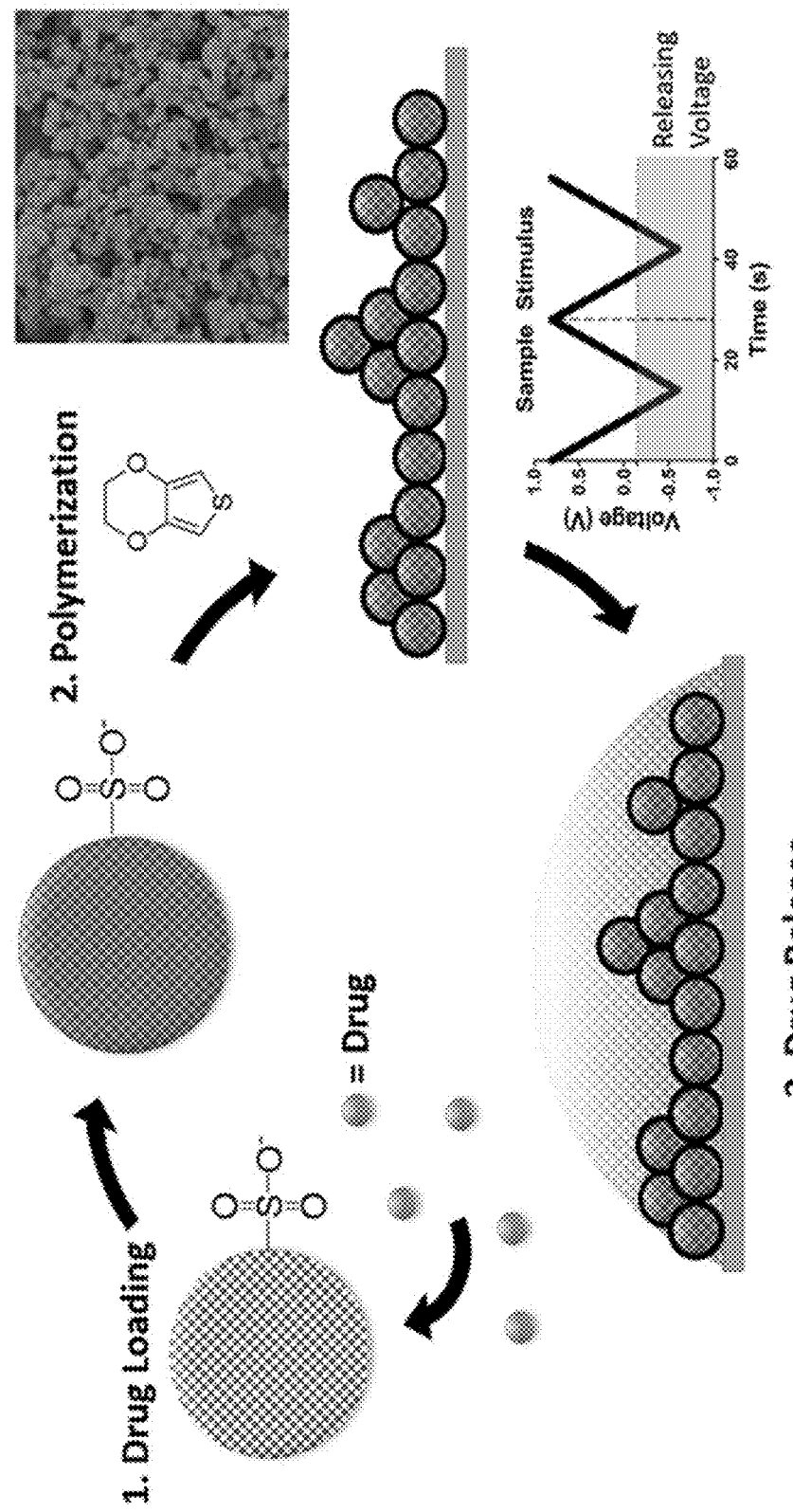
FIG. 2. Drug loading into SNP and Drug Release. Drugs are loaded into the porous nanoparticles via sonication. Loaded sulfonate nanoparticles are collected from solution by centrifuge then resuspended in an aqueous solution of EDOT. PEDOT/SNP films are polymerized under constant current, producing a film of polymer gated silica nanoparticles. Drug release is performed by triangular voltage pulses (cyclic voltammetry). Application of a sufficient reducing voltage results in drug release from the drug loaded PEDOT/SNP film.
Figure 11:
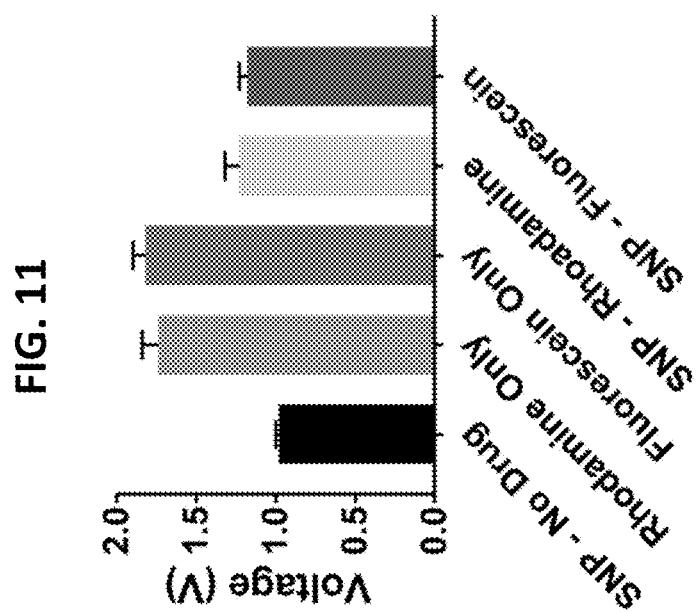

Drug loading and release from conducting polymers with electrical control offers a precise method for pharmacological delivery directly to the site of implantation on demand. Mesoporous SNP were employed for drug delivery due to their exceptionally high loading volume. Rhodamine and fluorescein were used as model drugs for quantifying drug release profile. Fluorescein has a negative charge while rhodamine-b is positively charged, and the combination of rhodamine and fluorescein allow for a better understanding of how oppositely charged compounds can be released from PEDOT/SNP films. The drug loading and release mechanism is depicted in FIG. 2. Nanoparticles were suspended in an aqueous solution of fluorescein, rhodamine, or a combination of both, and sonicated to encourage the entry of the dye into the pores. Loaded sulfonate nanoparticles are then collected from solution by centrifuge then resuspended in an aqueous solution of EDOT. PEDOT/SNP films are polymerized under constant current, producing a film of polymer gated silica nanoparticles. An immediate observation made was the ease of polymerization when the dye was loaded into SNPs prior to polymerization vs without SNPs, with electrode potential being substantially lower for electro-polymerization of drug loaded SNP (FIG. 11). After polymerization, electrodes coated with the dye-loaded composite were examined under a fluorescent microscope to observe the release in phosphate buffered saline (PBS) in real time (FIG. 12). A cyclic voltage sweep from 0.8V to −0.6V was used to trigger drug release from the coatings. We observed a halo of fluorescence surrounding the electrode upon stimulation, which dissipates within seconds of the end of stimulation. The quantified fluorescent intensity of the image was significantly higher during release than after for both rhodamine and fluorescein (FIG. 12B), indicating that both compounds were able to be loaded and released from the PEDOT/SNP film.

Figure 13B:
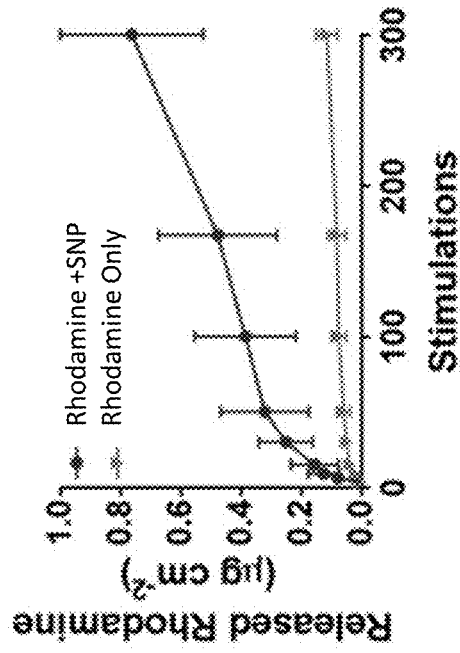
FIGS. 13A-13C. In vitro dye release from PEDOT/SNP coatings over the first 300 stimulations.
Figure 13A:
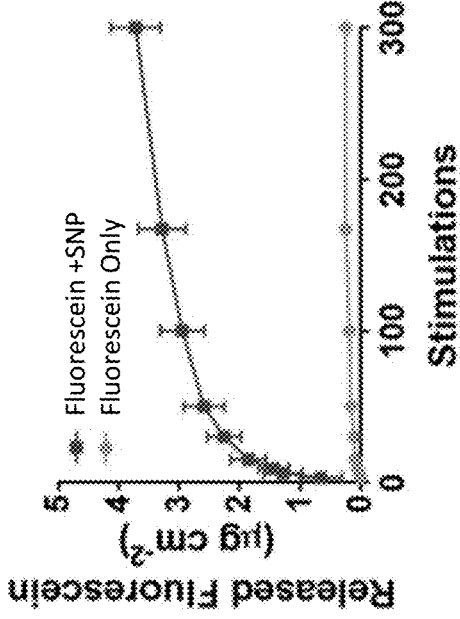
Figure 13C:
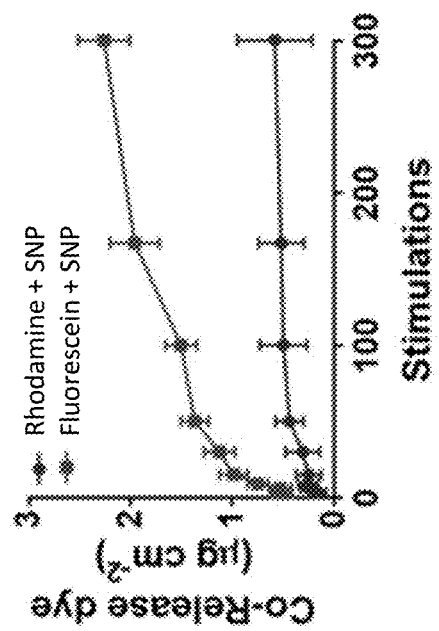

We further quantified the amount of release over number of stimuli from PEDOT/SNP composite and compared the performance to a control group of PEDOT loaded with the dye directly without the mesoporous SNP. Control and SNP dopant groups were polymerized to the same charge density. For both fluorescein and rhodamine, we observed a substantial increase in dye release over 9,000 and 5,000 stimulations relative to their respective control samples (FIGS. 6A, 6B), and the SNP doped polymers continued to release for up to 13,000 stimulations. To provide a higher resolution view of the release profile, release of compounds during the first 300 stimulations is included in the supplemental (FIG. 13). Note that drug release via diffusion quickly become negligible compared to the stimulated release. Overall drug loading was increased for both fluorescein (6.4×) and rhodamine (16.8×) when SNP were used as a reservoir (FIGS. 6D, 6E). This result indicates that SNP doping not only improve drug loading and release capacity, but also broaden the drug choice as majority of the previous conducting polymer drug release work focused on negatively charged drugs.

We account for the changes in drug loading and release by examining the published mechanisms of conducting polymer-based drug delivery.[3] In traditional conducting polymer-based drug delivery, negatively charged compounds (drugs) are incorporated to balance the positive charge formed along the polymer backbone during the oxidative polymerization. Positively charged compounds may also be loaded, instead relying on entrapment or interactions with other dopants. Controlled release from these films by alternating oxidative and reductive potentials proceeds through two mechanisms. First, reducing the film eliminates the charge-based interaction, allowing the trapped anionic compounds to exit of the conducting polymer matrix. Second, reduction and oxidation are accompanied with movement of ions and water in and out of the film, resulting in swelling/shrinking cycles of the polymer,[3] which further increases the diffusion of the drug out of the polymer. We speculate that the fluorescein release from the PEDOT/SNP coating occurs first when the film is reduced and the fluorescein exits the particle into the film and solution through diffusion and repulsion by the negative potential at the electrode. Rhodamine has a stronger electrostatic interaction with the negatively charged particle, slowing the release per stimulus. When the film is reduced, the volume change of the polymer and water influx encourages rhodamine to enter the neutral matrix, where it is then expelled during the subsequent oxidation as the film and dye repel each other.

Traditionally, each electrochemically controlled drug release experiment has been limited to one compound. This may be problematic if a drug therapy requires the use of two oppositely charged compounds. For example, co-administration of negatively charged acetylsalicylic acid (Aspirin), and the salts of ticlopidine[46, 47] and clopidogrel[47] have shown to reduce the occurrence of cardiac events following stenting. By loading a combination of fluorescein and rhodamine into SNP prior to polymerization, we could effectively load the film with 2 oppositely charged compounds (FIGS. 6C, 6F). Following CV stimulation, we observed a co-release of both compounds, albeit at slightly lower individual release of the compounds per stimulation, in addition to modified release profiles due to interactions between the two compounds. We demonstrated that through the use of SNP, we could load two oppositely charged compounds into one film for simultaneous release. With further optimization of the stimulation parameters for each compound, it may be possible to achieve selective release of co-loaded compounds.

2.5 Electrically Controlled Release of GABA and Glutamate

To further demonstrate the effectiveness of conductive polymer doped with negatively charged SNP for drug delivery, electrically stimulated release of the neurotransmitters glutamate and GABA from PEDOT/SNP coated electrodes was assessed. As discussed below, by pre-loading the drug molecules in SNP, the stimulated release is much more sustainable than PEDOT coating without SNP.

Figure 15:
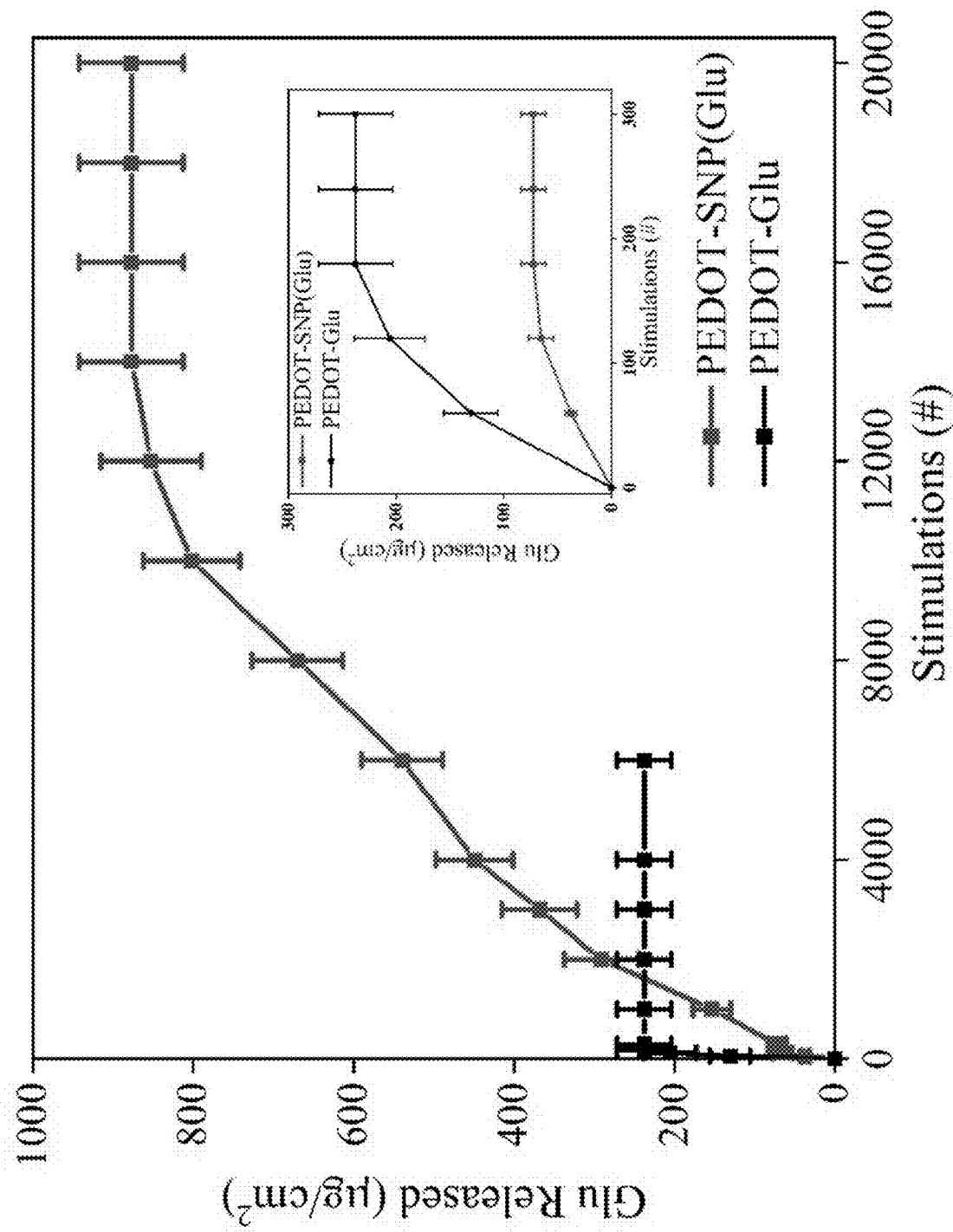
FIG. 15. Release profile of glutamate from two different drug-loaded conductive polymer coatings: PEDOT-SNP (Glu) (red) and PEDOT-Glu (black). Inset shows release profile of the first 300 stimulations. Glutamate (Glu) was either directly co-deposited with EDOT on platinum electrode surface (PEDOT-Glu) or preloaded to porous SNP first, and followed by co-deposition of PEDOT-SNP(Glu). The PEDOT-SNP(Glu) film with Glu preloaded to porous SNP provided a 78-fold increase in the number of stimulated release and 3.7-fold improvement in total drug releasing capacity relative to the PEDOT-Glu film.

First, the release profile of glutamate from two different drug-loaded films: PEDOT-SNP(Glu) and PEDOT-Glu, was assessed (FIG. 15). Glutamate (Glu) was either directly co-deposited with EDOT on platinum electrode surface (PEDOT-Glu) or preloaded to porous SNP first, and followed by co-deposition of PEDOT-SNP(Glu). For PEDOT-Glu film electrodeposition, 0.015 M EDOT was mixed with 700 mg/mL Glu solution. For PEDOT-SNP(Glu) electrodeposition, 0.015 M EDOT was mixed with 5 mg/mL SNP (Glu). For both depositions, a constant current 40 nA was applied to the Pt electrode for 250 s and a total charge density of 80 mC/cm$^2$ was passed. To trigger the release of Glu, a 2-Hz sine waveform (−0.6V-offset, 0.2V-amplitude) was applied to the PEDOT-Glu or PEDOT-SNP(Glu) coated electrodes immersed in 25 μl 1×PBS with a 0.5 cm Pt wire as the counter electrode. The solution was collected after every 60 (5 times), 1000 (4 times), and 2000 (8 times) stimulations and the Glu was quantified using an enzyme based glutamate sensor. The PEDOT-Glu film only worked for 180 stimulations with a maximum releasing capacity of 237±34 µg/cm². On the other hand, the PEDOT-SNP(Glu) film with Glu preloaded to porous SNP, was able be release Glu for up to 14000 stimulations with an improved total releasing capacity of 877±65 µg/cm². This is 78-fold increase in the number of stimulated release and 3.7-fold improvement in total drug releasing capacity.

Figure 16:
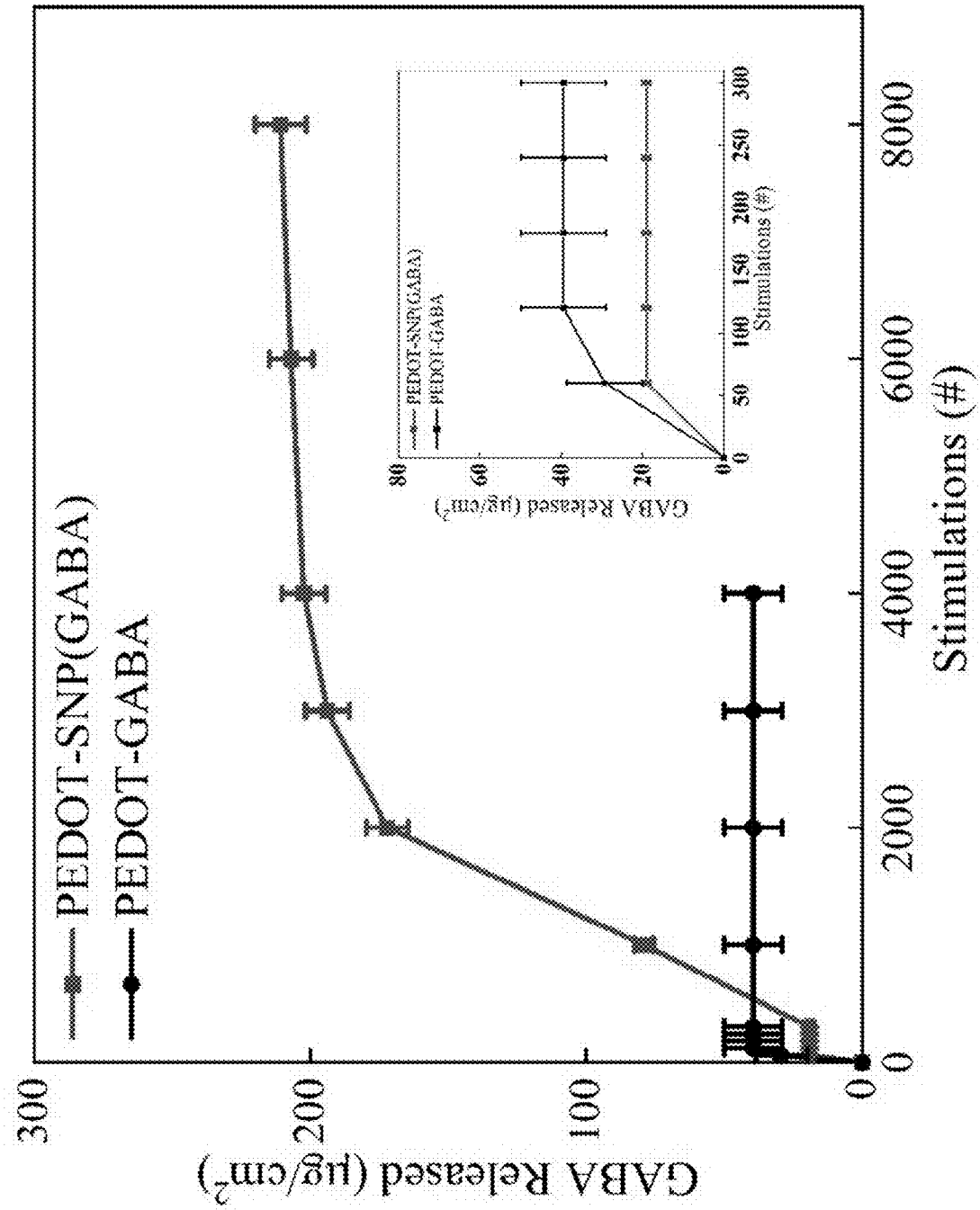
FIG. 16. Release profile of GABA from two different drug-loaded conductive polymer coatings: PEDOT-SNP (GABA) (red) and PEDOT-GABA (black). Inset shows release profile of the first 300 stimulations. GABA was either directly co-deposited with EDOT on platinum surface (PEDOT-GABA) or preloaded to porous SNP first, and followed by co-deposition of PEDOT-SNP(GABA). The PEDOT-SNP(GABA) film with GABA preloaded to porous SNP provided a 66-fold increase in number of stimulated release and 5.3-fold improvement in drug releasing capacity relative to the PEDOT-GABA.

Next, the release profile of GABA from two different drug-loaded films: PEDOT-SNP(GABA) and PEDOT-GABA, was assessed (FIG. 16). Inset shows release profile of the first 300 stimulations. GABA was either directly co-deposited with EDOT on platinum surface (PEDOT-GABA) or preloaded to porous SNP first, and followed by co-deposition of PEDOT-SNP(GABA). For electrodeposition of PEDOT-GABA film, 0.015 M EDOT was mixed with 1000 mg/mL GABA with PH adjusted to 12. For electrodeposition of PEDOT-SNP(GABA), 0.015 M EDOT was mixed with 5 mg/mL SNP(GABA). For both depositions, a constant current 40 nA was applied to Pt working electrodes for 250 s and a total charge density of 80 mC/cm² was passed. To trigger the release of GABA, a 2-Hz sine waveform (−0.6V-offset, 0.2V-amplitude) was applied to the PEDOT-GABA or PEDOT-SNP(GABA) coated electrodes immersed in 2.5 µl 1×PBS with a 0.5 cm Pt wire as the counter electrode. The solution was collected after every 60 (5 times), 1000 (4 times), and 2000 (twice) stimulations and samples incubated together with a 2.5 µl GABA fluorescent kit which quantify the GABA concentration by measuring fluorescent (resorufin). The PEDOT-GABA film released detectable GABA for 120 stimulations with a maximum releasing capacity of 40±10 µg/cm². Meanwhile, PEDOT-SNP(GABA) film with GABA preloaded to porous SNP was able to release GABA for >8000 stimulations with a total release of 211±9.3 µg/cm². This is a 66-fold increase in number of stimulated release and 5.3-fold improvement in drug releasing capacity.

2.6 Bioactivity of the Released Drug

Figure 7B:
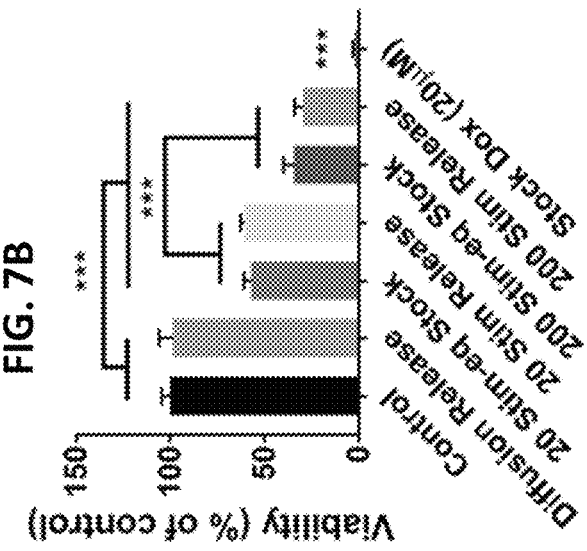
(FIG. 7B) 3T3 viability after incubation with DOX for 3 days.
Figure 7A:
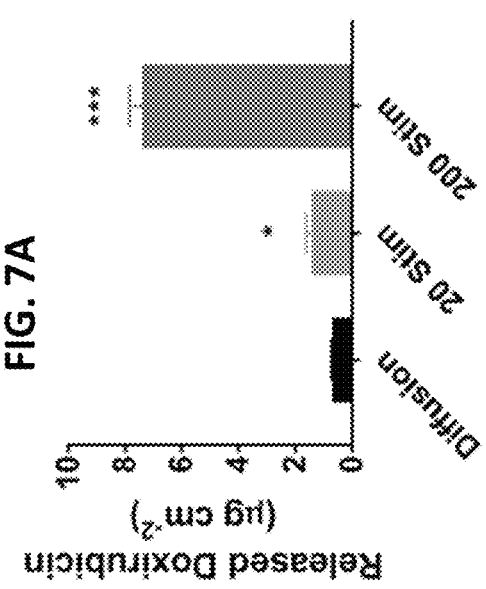
(FIG. 7A) Dox released from the PEDOT/SNP film.

Electrochemical methods of drug release may alter the activity of a compound due to the applied potentials, and it is therefore important to verify that the loading and release process doesn't compromise the drug's bioactivity. In order to assess the biological activity of released components, we loaded and released two bioactive compounds: Doxorubicin (Dox) and Melatonin. For Dox, a potent chemotherapeutic, release was performed for 0 (passive diffusion for 24 hours), 20, or 200 cycles into serum free DMEM. A small amount of diffusion release was observed from Dox loaded electrodes, as measured by absorbance at 280 nm. Electrical stimulation triggered significantly more release, with higher number of stimuli releasing more drug (FIG. 7A, 20 stimulations release 1.44 µg cm$^{-2}$ and 200 stimulations release 7.4 µg cm$^{-2}$). Released Dox was introduced to cultured 3T3 mouse fibroblast cells (FIG. 7B) and the toxicity was compared to freshly prepared Dox solution at the same concentration. After a 3-day incubation period, the viability of the 3T3 cells was evaluated with the XTT assay. No significant difference was observed between cells grown in standard culture media and the diffusion control group. Therefore, even though we detected a minute amount of Dox in the diffusion control, this quantity is below the toxic level. Released Dox from 20 and 200 stimulations significantly reduced the viability of cells from control, with the 200 stimulated release leading to higher toxicity compared to 20 stimulations. There was no difference in the effect of released Dox and the concentration-matched stock Dox, demonstrating the complete retainment of the bioactivity after electrochemical loading and release. Through this examination, we have demonstrated that not only does electrochemical release retain the viability of the drug, the drug quantity and effects can be tailored by the release parameters (stimulations) to impart predictable and scalable effects.

Figure 7D:
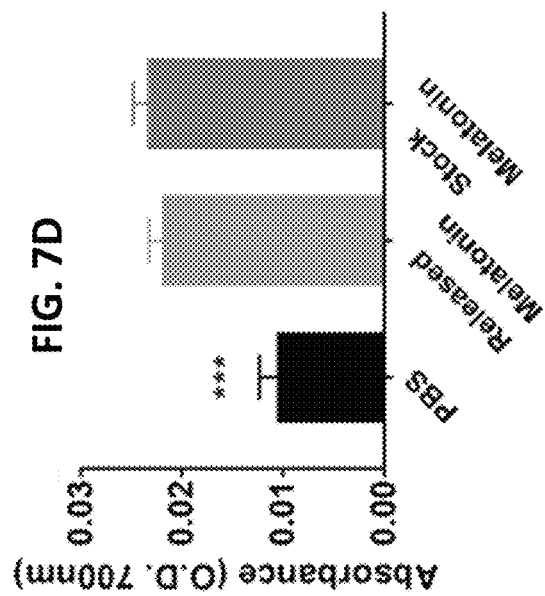
(FIG. 7D) Absorbance of $K_3[Fe(III)(CN)_6]$ after reduction by melatonin. *$p<0.05$ ***$p<0.001$.
Figure 7C:
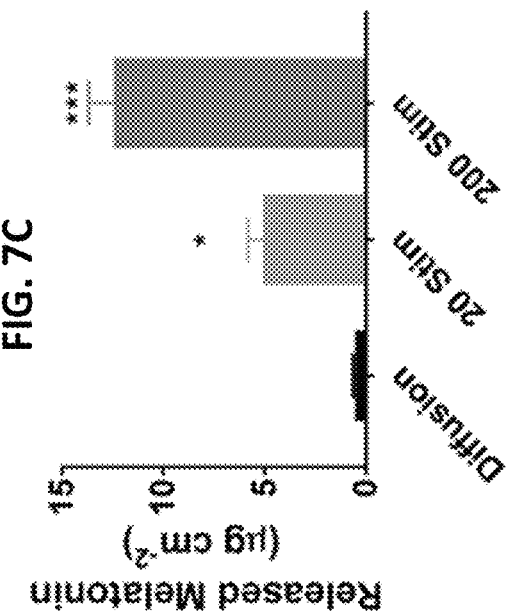
(FIG. 7C) Melatonin released from the PEDOT/SNP film.

Melatonin is an antioxidant and signaling molecule shown to minimize inflammation after injury. Recent work has demonstrated that melatonin is capable of preserving neuronal health around implanted neural electrodes and maintaining high recording quality over time when systemically administered daily.[48] This finding highly motivates the development of local delivery of melatonin from neural electrodes. However, melatonin presents additional difficulties for electrochemically driven drug delivery in that the compound is not electrochemically stable. With an oxidation potential at 0.65V vs Ag/AgCl,[49] melatonin is irreversibly deactivated by the oxidative potential required to polymerize PEDOT, which is generally larger than 0.8V. Here, we present a method of shielding the melatonin from the highly oxidative electropolymerization process by first loading the melatonin into porous SNPs. Melatonin loading was performed by sonicating the SNP in an ethanol solution of melatonin, and after drug loading the particles were thoroughly dried under vacuum to eliminate any remaining ethanol. Melatonin's solubility in water is substantially lower than the solubility in ethanol, this allowed for a high degree of loading into the SNP with minimal leakage during the short period of polymerization. Once in the film, melatonin was released by CV, such that the maximum voltage was never greater than 0.3V. The antioxidant capacity of the released melatonin was evaluated by $K_3[Fe(CN)_6]$ reduction assay.[50] The reduction reaction produced a dramatic color change, which was recorded at 700 nm (FIG. 7D). We demonstrate here that released melatonin and stock melatonin were both capable of producing a significant change in the absorbance of the solution at 700 nm, and demonstrate that the released melatonin had maintained its antioxidant capacity. The retention of melatonin's antioxidant abilities might be attributed to the non-conductive nature of the silica nanoparticles, minimizing electrochemically driven reactions to the loaded drug.

2.7 In Vivo Proof of Concept Drug Release Demonstration

Different types of microelectrodes, either a platinum iridium microwire or carbon fiber, were coated with PEDOT/SNP for in vivo release testing. A craniotomy was performed on a wild-type mouse which was then placed under a two-photon microscope for imaging. A bone screw counter and Ag/AgCl reference were placed in contact with the brain. A fluorescein loaded PEDOT/SNP coated Pt/Ir electrodes was inserted and used to visualize drug release in brain tissue in real time (FIG. 8A). CV was performed to initiate the release of the dye, and the peak change in fluorescence was calculated (FIG. 8B). After release, the dye dissipated into the surrounding tissues within several seconds. The release and dispersal of the fluorescein dye demonstrates controllable release and the diffusion profile of released compounds in vivo.

Next, we aimed to modulate cellular activity by release of the glutamate AMPA/Kainate receptor antagonist 6,7-dinitroquinoxaiine-2,3-dione (DNQX). DNQX is a small, negatively charged compound that blocks glutamate transmission. We have previously observed that DNQX may be loaded and electrically released from PEDOT/CNT films in vivo and produce a transient (<6 second) inhibition of sensory evoked neural activity recorded in barrel cortex of rats.[9] In this study, DNQX release from PEDOT/SNP was assessed using a GCaMP mouse model. The GCaMP fluorescence is tied directly to intracellular calcium activity, such that when neurons fire action potentials, the calcium influx cause GCaMP to produce a bright green fluorescence.

In order to minimize tissue damage during insertion, a carbon fiber electrode (D=7 μm) was used for DNQX release. DNQX loaded PEDOT/SNP was polymerized on a carbon fiber electrode and implanted in the mouse brain, proximal to the midline and motor cortex, and CV stimulation was performed to release DNQX from the polymer. We then compared the fluorescence intensity of the tissues prior to and during DNQX release (FIG. 8F), and observed a significant decrease in the fluorescence intensity when the electrode was receiving a reducing potential. A control experiment was performed by inserting a PEDOT/SNP electrode without DNQX loading. No change in fluorescent activity was observed in the absence of DNQX (FIG. 8E). Qualitatively, a difference in neural firing was noted by examining the standard deviation of Z-projection prior to and during stimulation. This projection examines how pixels deviate over time, displaying pixels with higher deviations as brighter. Cell firing events produce greater deviations in pixel intensity, and the compression allows for a single frame representation of the GCaMP activity over the course of the imaging. We observed a higher number of active cells during the pre-stimulation period (FIG. 8G) than during the DNQX release (FIG. 8H), with only small amounts or residual GCaMP activity present during release. From these experiments, we conclude that PEDOT/SNP was able to release DNQX upon electrical stimulation and the released DNQX was capable of modulating neural activity localized to the electrode, demonstrating the feasibility and potential of the PEDOT/SNP based drug delivery platform.

2.8 Stability of PEDOT/SNP Coatings

Delamination of conducting polymers from the electrode site is one of most common and detrimental issue experienced after polymerization. Removal of the coating eliminates the electrochemical and drug delivery properties of the coatings, while potential causing damage due to a second foreign body being present in the tissues. Accordingly, the stability of two dopants for PEDOT, polystyrenesulfonate, and the sulfonate nanoparticles described herein, were examined on gold electrodes. These films were tested by sonication, for 10, 30, 60 minutes. The impedances, measured at 1 Hz, and charge storage capacities were measured to examine changes in polymer adhesion to the gold surface.

Figure 14:
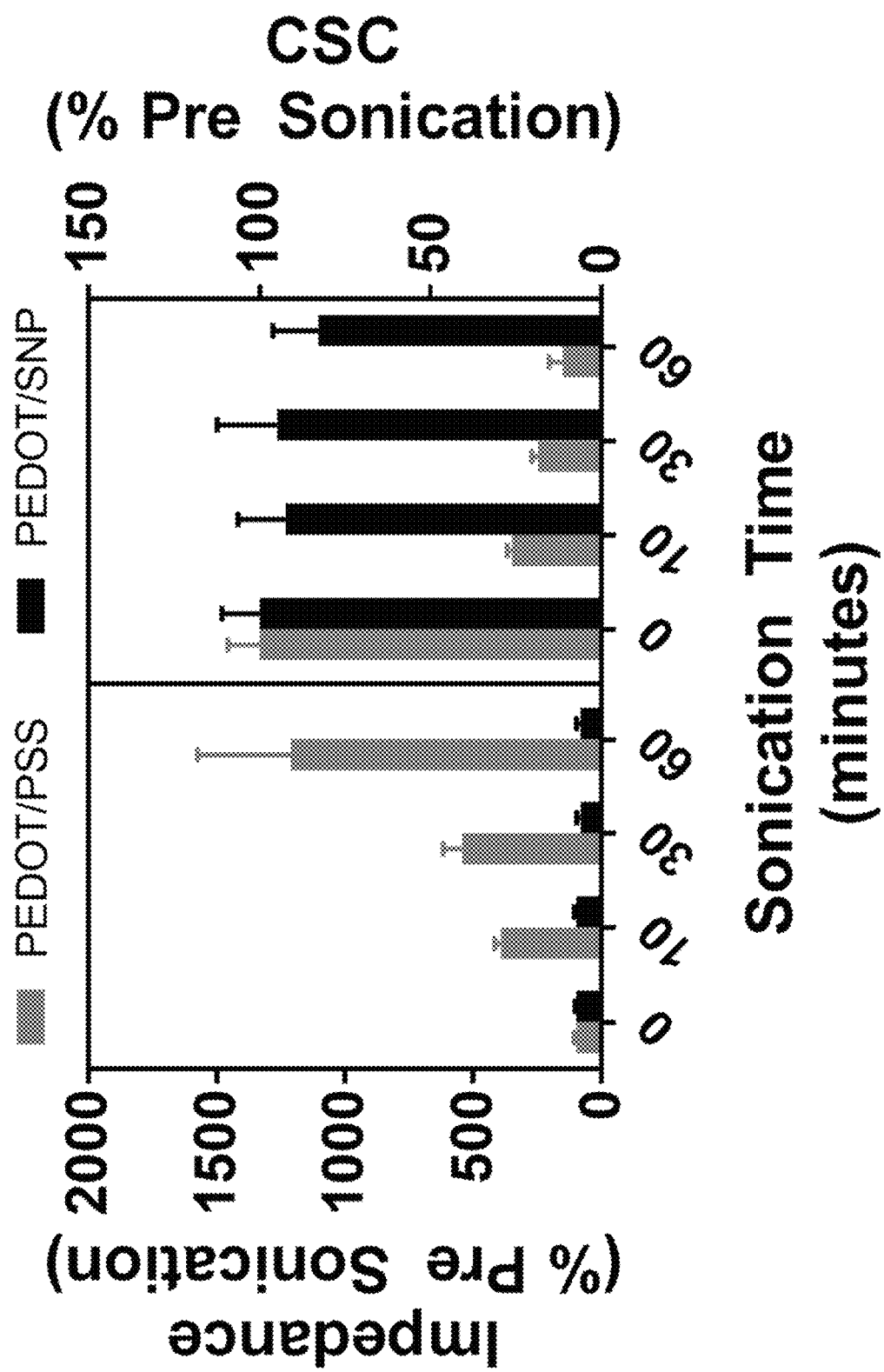
FIG. 14. Changes in the impedance and charge storage capacity of electrodes after sonication for 10, 30, and 60 minutes. PEDOT doped with PSS or SNP was deposited on bare gold electrodes. Impedance of PEDOT/PSS dramatically increases with sonication, while PEDOT/SNP remains at or around pre-sonication values. CSC of PEDOT/PSS decreases with increasing sonication times, while PEDOT/SNP maintains its charge storage capabilities.

It was observed that the PEDOT/PSS groups is readily damaged by the sonication treatment. The sonication of PEDOT/PSS resulting in a 1000% increase in impedance, and near complete elimination of its CSC (FIG. 14). SNP doped PEDOT was more stable, maintaining its impedance and charge storage throughout the sonication. Similar to electrochemical stability experiments, we attribute this change in mechanical stability to the nanoparticle dopants. While PEDOT is brittle, the SNP are capable of internally stabilizing the film.

3. Conclusions

Conducting polymers are at the forefront of biomaterials research with applications in biosensors, bioelectronics, tissue engineering scaffolds and drug delivery systems. Through the use of nanoparticle-based dopants, we have demonstrated the synthesis of a novel class of conducting polymer composites. The material properties can be fine-tuned by adjusting the nanoparticle dopants. Solid nanoparticle doped PEDOT possesses impressive electrochemical characteristics, including low impedance, high charge storage capacity and charge injection limit among the best reported in advanced electrode coatings. This polymer demonstrates its potential as a stimulating electrode coating by maintaining stability for over 4.3 million stimulations. By exchanging the solid nanoparticles for mesoporous particles, we can effectively incorporate a reservoir for drug delivery. Unlike many other electrochemical drug delivery platforms, we have demonstrated that multiple oppositely charge compounds can be loaded into a single film, and that electroactive compounds can be electrochemically loaded and released while maintaining their bioactivity in vitro and in vivo. Finally, the nanoparticles doping facilitate adhesion between the polymer and electrode, greatly improving mechanical stability. Taken together, the nanoparticle dopant approach offers endless new opportunities for designing new conducting polymers composite to suite the need of various biomedical applications.

4. Experimental Selection

Materials and Characterization

All materials were purchased from Sigma Aldrich and used as received unless otherwise stated. Transmission electron microscopy (TEM) images were taken by Joel JEM2100f. Scanning electron microscopy (SEM) were taken by JSM6355F. Dynamic light scattering and ζ-potential measurements were performed with Malvern ZS90 Zetasizer. Electrochemical polymerization, analysis, and release were performed by Autolab (PGSTAT128N). Spectroscopic measurements were performed on Molecular Devices SpectraMax i3x. Fluorescence imaging was performed on Leica, DMI4000 B fluorescent scope. Two-photon imaging was performed on an Ultima IV, Prairie Technologies Thiolated Silica-Nanoparticle Synthesis Thiol modified silica nanoparticles synthesis was adapted from Moeller et al.[42] In brief, a solution comprising of water (36 mL), ethanol (5 mL), hexadecyl trimethyl-ammonium bromide (CTAB, 1.3 g), and triethanolamine (6.18 mL) were mixed for 30 minutes and heated to 60° C. CTAB was excluded from the synthesis of non-porous particles. To this mixture, Tetraethyl orthosilicate (3 mL) was added dropwise, followed by 1 mL of mercaptopropyl trimethoxysilane (MTS). A second aliquot of MTS (100 μL) was added after 1 hour. The reaction proceeded for 2 hours, then was cooled and the particles collected by centrifuge (20,000 rpm×10 minutes). Surfactant template was removed by washing in water, ethanol, then by heating the particles ethanol (100 ml) with HCl (2.5M) under reflux at 70° C. for 10 hours. Particles were then collected and washed in water.

Oxidation of Thiol to Sulfonate

Two grams of thiol modified particles were suspended in $H_2O_2$ (20%, 25 ml), followed by the addition of $H_2SO_4$ (20 μL). After oxidation, particles were collected by centrifuge and washed with water. Resulting SNP were colloidally stable and stored at 4° C. until used.

Electropolymerization

Polymerizations were carried out with a three-electrode set-up with a platinum foil counter and Ag/AgCl reference. EDOT (0.01M) in DI-water was mixed with SNP (5 mg $ml^{-1}$) and sonicated for 5 minutes in a bath sonicater. Electrode materials varied by experiment, but all polymerizations were carried out under constant current (320 μA $cm^{-2}$).

Electrochemical Characterization

All electrochemical characterizations were performed in triplicate on 3 separate gold electrodes wire electrodes (50 μm diameter, A-M systems). Electrochemical Impedance Spectroscopy (EIS) was measured from 1 Hz to 100 kHz. Cyclic voltammetry was measured from −0.9 to 0.5V at 100 mV s$^{-1}$. Charge storage capacity was calculated as the integral of the 3$^{rd}$ scan of the CV, where I is the current and A is the area of the electrode.

$$CSC = \frac{\int |I| dt}{A}$$

Charge injection limit is defined as the amount of injectable charge prior to a voltage transient exceeding −0.6V divided by the area of the electrode. An anodic leading biphasic pulse of 1 ms per phase with a 200 µs interphase delay was used. Charge injection was then calculated as:

$$CIL = \left|\frac{I \times t}{A}\right|$$

such that |V| resulting from I is less than 0.6V. Access voltage was subtracted from the calculation.

Biocompatibility

Highly aggressive proliferating Immortalized (HAPI) microglia cells were used as a model for testing the biocompatibility of PEDOT/SNP. Gold electrodes were prepared by sputter-coating gold (100 nm) onto a polypropylene sheet with an adhesive mask. The mask was removed to create circular electrodes of 7.5 mm diameter. Samples were prepared by electropolymerizing SNP or polystyrene sulfonate doped PEDOT under constant current to a charge density of 75 mC cm$^{-2}$. Polymerized electrodes were trimmed to fit into a 48-well plate (Falcon). Samples were sterilized by soaking in 70% ethanol for 15 minutes followed by drying and exposure to UV for 15 minutes. HAPI cells were plated over the polymer samples at a density of 15,000 cells per well. Control cells were grown on tissue culture polystyrene (TCPS). Cells were grown for 2 days (semi-confluent), positive controls were treated with 0.2% Triton-X 4 hours prior to measuring the viability with an XTT assay. 5 samples each of PEDOT/SNP, PEDOT/PSS, and positive and negative controls were prepared for testing, and the assay repeated 3 times to ensure reproducibility.

XTT assay was performed as directed by the distributer. In brief, 2,3-Bis-(2-Methoxy-4-Nitro-5-Sulfophenyl)-2H-Tetrazolium-5-Carboxanilide (XTT, Invitrogen, 1 mg ml$^{-1}$) was added to culture media. 10 µl of phenazine methosulfate (PMS, 10 mM) was added to XTT/media solution (4 ml) just prior to the addition of XTT solution (50 uL) per well. Cells were incubated for 3 hours and the absorbance of the supernatant was measured at 450 nm. HAPI cells were imaged with a Live/Dead assay (Invitrogen). Supernatant solution was removed and replaced with 1/1000 dilutions for Propidium Iodide and Calcein AM in PBS. Cells were incubated for 1 hour and imaged with fluorescence microscopy.

Drug Loading

Drug compounds (25 mg ml$^{-1}$) were dissolved at in water (for rhodamine, fluorescein, dox, and DNQX) or ethanol (melatonin). 5 mg of mesoporous SNP were sonicated with 200 µl of drug solution for 20 minutes prior to the particles being collected by centrifuge and dried under vacuum.

Electropolymerization and Drug Release 5 mg of drug loaded particles were suspended in 3 ml of EDOT (0.01M) solution in water. Electropolymerization was carried out for 200 seconds on 2 mm diameter gold electrodes or 70 µm diameter Pt/Ir wires (A-M systems, 90/10 Pt/Ir). Electrodes were then washed with PBS on an orbital shaker for 2 hours then soaked overnight to remove any adsorbed drugs. Drug release was performed with cyclic voltammetry between −0.6V and 0.8V at 1V s$^{-1}$ for dye release, −0.6 to 0.8V at 100 mV s$^{-1}$ for DOX and DNQX release, or from −0.6 to 0.3V at 100 mV s$^{-1}$ for melatonin, into 3 ml of PBS or the animal model.

In Vitro Activity

Dox was loaded and released from PEDOT/SNP films as described above. 3T3 cells were cultured in 48 well plates for 2 days to reach semi-confluency, at which point the culture media was removed and replaced with serum-free media containing stock dox, released dox, or no dox. Cells were culture for 72 h, at which point the media was aspirated and the viability of the cells measured with XTT assay as described above.

Released melatonin was examined for antioxidant capabilities through a Prussian blue assay. 1 ml of PBS containing released melatonin was added to 1 mL of K$_3$[Fe(CN)$_6$] (1%, 30 mM) and incubated at 50° C. for 20 minutes. 1 mL of solution was removed and added to 0.8 mL of water, followed by the addition of 200 µL of FeCl$_3$(0.01%, 6 µM), creating a deep blue dye. The absorbance of the resulting solution was measured at 700 nm.

In Vivo Drug Release

Platinum iridium wire electrodes were created by cutting 8 cm sections of 70 µm diameter Pt/Ir (90/10) wire and de-insulating 1 mm at the tip. The tip was cut at a 30° angle to sharpen. The opposite end was connected to a gold pin via silver epoxy to facilitated interfacing with electronic equipment. Carbon fiber electrodes were constructed by pulling a 7 um carbon fiber through a glass capillary which was then filled with mercury to form the electrical connection. Drug loading was performed as described above, adjusting current to match the exposed surface area. Polymer was deposited at a density of 100 mC cm$^{-1}$.

All animal work was performed under the guidelines of the University of Pittsburgh Institutional Animal Care and Use Committee (IACUC). Wildtype C57-BL6 mice were used to observe fluorescein release, while Thy1-GCaMP mice were used to visualize neural activity during DNQX release. Animals were anesthetized with ketamine (75 mg/kg) and xylazine (7.5 mg/kg). A cranial window was created, following which the animal was placed under the two-photon microscope for electrode insertion and imaging. Imaging The electrode was inserted at 30° from parallel to the table, with care taken to minimize bleeding. and drug release were performed on awake animals to minimize the effect of anesthesia on neural activity. Release was performed in 3 steps. First, a 2-minute baseline was recorded. This was followed by 10 drug release stimulations with a 30 second delay between subsequent stimulations. In vivo drug release was performed by cyclic voltammetry scans from 0.8V to −0.6V vs a Ag/AgCl reference electrode. Following 10 cycles of stimulation, a final 2-minute baseline recording was performed Calculations of fluorescence are made by first masking the electrode. A background fluorescence was determined by averaging all frames together, allowing for representation of small time windows as the % change vs the background intensity as shown below.

$$\Delta f = \frac{f_{ave} - f_{background}}{f_{background}} \times 100\%$$

The inter-pulse fluorescence was determined by Δf during the reducing voltage, and comparing this to the Δf during the prior oxidative voltage (V>−0.2).

Statistics

Unless otherwise stated, statistical significance was measured via one-way ANOVA with Tukey's post hoc. Significance of FIG. 3B and FIG. 4I were determined via two-way ANOVA. Significance of FIGS. 8E,F was determined via two-tailed paired T-Test. Statistical analysis was performed in GraphPad Prism 7.03.

REFERENCES FOR EXAMPLE 1

[1] Pickup et al., In vivo molecular sensing in diabetes mellitus: an implantable glucose sensor with direct electron transfer, Diabetologia 32(3) (1989) 213-217.
[2] Chen et al., Recent advances in electrochemical sensing for hydrogen peroxide: a review, Analyst 137(1) (2012) 49-58.
[3] Svirskis et al., Electrochemically controlled drug delivery based on intrinsically conducting polymers, Journal of Controlled Release 146(1) (2010) 6-15.
[4] Collinger et al., High-performance neuroprosthetic control by an individual with tetraplegia, The Lancet 381 (9866) (2013) 557-564.
[5] Flesher et al., Intracortical microstimulation of human somatosensory cortex, Science Translational Medicine 8(361) (2016) 361ra141.
[6] Martin, Molecular design, synthesis, and characterization of conjugated polymers for interfacing electronic biomedical devices with living tissue, MRS Communications 5(2) (2015) 131-153.
[7] Woeppel et al., Recent advances in neural electrode-tissue interfaces, Current Opinion in Biomedical Engineering 4(Supplement C) (2017) 21-31.
[8] Guimard et al., Conducting polymers in biomedical engineering, Progress in Polymer Science 32(8) (2007) 876-921.
[9] Zhanhong et al., Electrically Controlled Neurochemical Release from Dual-Layer Conducting Polymer Films for Precise Modulation of Neural Network Activity in Rat Barrel Cortex, Advanced Functional Materials 28(12) (2017) 1703988.
[10] Cui et al., Electrochemical deposition and characterization of conducting polymer polypyrrole/PSS on multichannel neural probes, Sensors and Actuators A: Physical 93(1) (2001) 8-18.
[11] Kozai et al., Chronic In Vivo Evaluation of PEDOT/ CNT for Stable Neural Recordings, IEEE Transactions on Biomedical Engineering 63(1) (2016) 111-119.
[12] Cui and Martin, Electrochemical deposition and characterization of poly(3,4-ethylenedioxythiophene) on neural microelectrode arrays, Sensors and Actuators B: Chemical 89(1) (2003) 92-102.
[13] Luo et al., Highly stable carbon nanotube doped poly (3,4-ethylenedioxythiophene) for chronic neural stimulation, Biomaterials 32(24) (2011) 5551-5557.
[14] Kip et al., Poly(3,4-ethylenedioxythiophene) (PEDOT) polymer coatings facilitate smaller neural recording electrodes, Journal of Neural Engineering 8(1) (2011) 014001.
[15] Kozai et al., Ultrasmall implantable composite microelectrodes with bioactive surfaces for chronic neural interfaces, Nature Materials 11 (2012) 1065.
[16] Chen et al., PEDOT/MWCNT composite film coated microelectrode arrays for neural interface improvement, Sensors and Actuators A: Physical 193 (2013) 141-148.
[17] Venkatraman et al., In Vitro and In Vivo Evaluation of PEDOT Microelectrodes for Neural Stimulation and Recording, IEEE Transactions on Neural Systems and Rehabilitation Engineering 19(3) (2011) 307-316.
[18] Lu et al., Electrodeposited polypyrrole/carbon nanotubes composite films electrodes for neural interfaces, Biomaterials 31(19) (2010) 5169-5181.
[19] Zheng et al., Soft Conducting Elastomer for Peripheral Nerve Interface, Advanced Healthcare Materials 0(0) (2019) 1801311.
[20] Vlamidis et al., Electrodeposition of PEDOT perchlorate as an alternative route to PEDOT:PSS for the development of bulk heterojunction solar cells, Journal of Solid State Electrochemistry 19(6) (2015) 1685-1693.
[21] King et al., Structural, chemical and electrochemical characterization of poly(3,4-Ethylenedioxythiophene) (PEDOT) prepared with various counter-ions and heat treatments, Polymer 52(5) (2011) 1302-1308.
[22] Stauffer and Cui, Polypyrrole doped with 2 peptide sequences from laminin, Biomaterials 27(11) (2006) 2405-2413.
[23] Hernández et al., Template Fabrication of Protein-Functionalized Gold-Polypyrrole-Gold Segmented Nanowires, Chemistry of Materials 16(18) (2004) 3431-3438.
[24] Kum et al. Mulchandani, Biomolecules-carbon nanotubes doped conducting polymer nanocomposites and their sensor application, Talanta 74(3) (2007) 370-375.
[25] Thompson et al.Wallace, Effect of the dopant anion in polypyrrole on nerve growth and release of a neurotrophic protein, Biomaterials 32(15) (2011) 3822-3831.
[26] Serra Moreno et al., Polypyrrole-polysaccharide thin films characteristics: Electrosynthesis and biological properties, Journal of Biomedical Materials Research Part A 88A(3) (2009) 832-840.
[27] Campbell et al., Incorporation of Erythrocytes into Polypyrrole to Form the Basis of a Biosensor to Screen for Rhesus (D) Blood Groups and Rhesus (D) Antibodies, Electroanalysis 11(4) (1999) 215-222.
[28] Gomez and Schmidt, Nerve growth factor-immobilized polypyrrole: Bioactive electrically conducting polymer for enhanced neurite extension, Journal of Biomedical Materials Research Part A 81A(1) (2007) 135-149.
[29] Catt et al., Self-powered therapeutic release from conducting polymer/graphene oxide films on magnesium, Nanomedicine: Nanotechnology, Biology and Medicine 14(7) (2018) 2495-2503.
[30] Weaver et al., Electrically Controlled Drug Delivery from Graphene Oxide Nanocomposite Films, ACS Nano 8(2) (2014) 1834-1843.
[31] Wadhwa et al., Electrochemically controlled release of dexamethasone from conducting polymer polypyrrole coated electrode, Journal of Controlled Release 110(3) (2006) 531-541.
[32] Abidian et al., Conducting-Polymer Nanotubes for Controlled Drug Release, Advanced Materials 18(4) (2006) 405-409.
[33] Luo and Cui, Electrochemically controlled release based on nanoporous conducting polymers, Electrochemistry Communications 11(2) (2009) 402-404.
[34] Proctor et al., Electrophoretic drug delivery for seizure control, Science Advances 4(8) (2018) eaau1291.

[35] Simon et al., Organic electronics for precise delivery of neurotransmitters to modulate mammalian sensory function, Nature Materials 8 (2009) 742.
[36] Lai et al., A Mesoporous Silica Nanosphere-Based Carrier System with Chemically Removable CdS Nanoparticle Caps for Stimuli-Responsive Controlled Release of Neurotransmitters and Drug Molecules, Journal of the American Chemical Society 125(15) (2003) 4451-4459.
[37] Lee et al., Simple Synthesis of Functionalized Superparamagnetic Magnetite/Silica Core/Shell Nanoparticles and their Application as Magnetically Separable High-Performance Biocatalysts, Small 4(1) (2008) 143-152.
[38] Woeppel et al., Enhancing surface immobilization of bioactive molecules via a silica nanoparticle based coating, Journal of Materials Chemistry B 6(19) (2018) 3058-3067.
[39] Gupta et al., Silica functionalized sulfonic acid catalyzed one-pot synthesis of 4,5,8a-triarylhex-ahydropyrimido[4,5-d]pyrimidine-2,7(1H,3 H)-diones under liquid phase catalysis, Journal of the Brazilian Chemical Society 21 (2010) 349-354.
[40] He and Shi, Mesoporous silica nanoparticle based nano drug delivery systems: synthesis, controlled drug release and delivery, pharmacokinetics and biocompatibility, Journal of Materials Chemistry 21(16) (2011) 5845-5855.
[41] Slowing et al., Mesoporous Silica Nanoparticles for Reducing Hemolytic Activity Towards Mammalian Red Blood Cells, Small 5(1) (2009) 57-62.
[42] Möller et al., Colloidal Suspensions of Nanometer-Sized Mesoporous Silica, Advanced Functional Materials 17(4) (2007) 605-612.
[43] Cogan et al., In vitro comparison of the charge-injection limits of activated iridium oxide (AIROF) and platinum-iridium microelectrodes, IEEE Transactions on Biomedical Engineering 52(9) (2005) 1612-1614.
[44] Wang, et al., Neural Stimulation with a Carbon Nanotube Microelectrode Array, Nano Letters 6(9) (2006) 2043-2048.
[45] Harish et al., Barrier films to control loss of 9,10-anthraquinone-2-sulphonate dopant from PEDOT films during electrochemical transitions, Electrochimica Acta 54(13) (2009) 3618-3622.
[46] Leon et al., A Clinical Trial Comparing Three Antithrombotic-Drug Regimens after Coronary-Artery Stenting, New England Journal of Medicine 339(23) (1998) 1665-1671.
[47] Bertrand et al. Investigators, Double-Blind Study of the Safety of Clopidogrel With and Without a Loading Dose in Combination With Aspirin Compared With Ticlopidine in Combination With Aspirin After Coronary Stenting, Circulation 102(6) (2000) 624-629.
[48] Golabchi et al., Melatonin improves quality and longevity of chronic neural recording, Biomaterials 180 (2018) 225-239.
[49] Xiao-Ping et al., Study on the Electrochemical Behavior of Melatonin with an Activated Electrode, Electroanalysis 14(23) (2002) 1654-1660.
[50] Gulcin et al., On the in vitro antioxidative properties of melatonin, Journal of Pineal Research 33(3) (2002) 167-171.
[51] Kozai et al., Chronic In Vivo Evaluation of PEDOT/CNT for Stable Neural Recordings, IEEE Transactions on Biomedical Engineering 63(1) (2016) 111-119.
[52] Miriani et al., Cytotoxic analysis of the conducting polymer PEDOT using myocytes, 2008 30th Annual International Conference of the IEEE Engineering in Medicine and Biology Society, 2008, pp. 1841-1844.

It will be apparent that the precise details of the methods or compositions described may be varied or modified without departing from the spirit of the described embodiments. We claim all such modifications and variations that fall within the scope and spirit of the claims below.

We claim:

1. A coated electrode comprising a coating of a conductive polymer doped with negatively charged silica nanoparticles on a conductive surface of the electrode.

2. The coated electrode of claim 1, wherein the conductive polymer is poly 3,4 ethylene dioxythiophene (PEDOT).

3. The coated electrode of claim 1, wherein the negatively charged silica nanoparticles are sulfonated silica nanoparticles.

4. The coated electrode of claim 1, wherein the negatively charged silica nanoparticles are from about 10 to about 500 nm in diameter.

5. The coated electrode of claim 1, wherein the coating is formed by electropolymerization of a mixture of monomers of the conductive polymer and the negatively charged silica nanoparticles onto a conductive surface of the electrode.

6. The coated electrode of claim 5, wherein the coating is formed by electropolymerization of a mixture of 3,4 ethylene dioxythiophene (EDOT) monomers and the negatively charged silica nanoparticles onto a conductive surface of the electrode.

7. The coated electrode of claim 1, wherein the coating on the electrode is from 25 mC cm$^{-2}$ to 2 C cm$^{-2}$ as measured during electrodeposition.

8. The coated electrode of claim 1, wherein the electrode is a gold, platinum, iridium, glassy carbon, steel, tungsten, magnesium, or carbon fiber electrode.

9. The coated electrode of claim 1, wherein the negatively charged silica nanoparticles are mesoporous.

10. The coated electrode of claim 9, wherein the mesoporous negatively charged silica nanoparticles comprise pores with an average diameter of from about 1 nm to about 20 nm.

11. The coated electrode of claim 10, wherein the mesoporous negatively charged silica nanoparticles are formed by a process comprising incubating silica precursors and a surfactant under conditions sufficient to form the mesoporous negatively charged silica nanoparticles.

12. The coated electrode of claim 11, wherein the surfactant is hexadecyl trimethylammonium bromide (CTAB), hexadecyl trimethylammonium chloride (CTACL), Triton-X, or a poly(ethylene-oxide) derivative.

13. A coated electrode comprising a coating of a conductive polymer doped with negatively charged silica nanoparticles on a conductive surface of the electrode, wherein the negatively charged silica nanoparticles are mesoporous and loaded with a pharmaceutical agent.

14. The coated electrode of claim 13, wherein the pharmaceutical agent is a small molecule drug.

15. The coated electrode of claim 13, wherein the pharmaceutical agent is an anti-oxidant, an anti-inflammatory agent, an anti-convulsant agent, an anti-bacterial agent, or an anti-cancer agent.

16. The coated electrode of claim 13, wherein the pharmaceutical agent is any one of: melatonin, dexamethasone, minocycline, glutamate, GABA, muscimol, bicuculline, AP-5 (amino-5-phosphonovaleric acid), 6,7-dinitroquinoxaline-2,3-dione (DNQX), 6-cyano-7-nitroquinoxaline-2,3-dione, doxorubicin.

17. The coated electrode of claim 1, wherein impedance and charge storage capacity of the coated electrode remains stable following sonication for 60 minutes.

18. A medical implant comprising the coated electrode of claim 1.

19. The medical implant of claim 18, wherein the medical implant is a cardiac pacemaker, a cardiac defibrillator, a deep brain stimulator, a cochlear implant, a peripheral nerve stimulator, a spinal cord stimulator, a neural electrode, an enteric nervous system stimulator, a skin surface electrode (such as ECG, EMG and EEG electrode), an intramuscular electrode, or an implantable glucose sensor.

20. A method of making the coated electrode of claim 1, comprising:
incubating a mixture of monomers of a conductive polymer and negatively charged silica nanoparticles with a conductive surface of an electrode; and
applying a potential sufficient to oxidize and polymerize the monomers on the conductive surface of the electrode to form a coating of the conductive polymer doped with the negatively charged silica nanoparticles at the conductive surface of the electrode;
thereby forming the coated electrode comprising a coating of a conductive polymer doped with negatively charged silica nanoparticles.

21. The method of claim 20, wherein the monomers of the conductive polymer are 3,4 ethylene dioxythiophene (EDOT) monomers and the method forms the coated electrode comprising a coating of poly-3,4 ethylene dioxythiophene (PEDOT) doped with negatively charged silica nanoparticles.

22. The method of claim 20, the method further comprising making the negatively charged silica nanoparticles, comprising:
incubating silica precursors under conditions sufficient to form silica nanoparticles, wherein the silica precursors comprise one or more thiol functional groups, thereby forming thiol modified silica nanoparticles; and
oxidizing the thiol functional groups of the thiol modified silica nanoparticles to form sulfonated silica nanoparticles, thereby forming the negatively charged silica nanoparticles.

23. The method of claim 22, wherein the negatively charged silica nanoparticles are mesoporous, wherein incubating the silica precursors under the conditions sufficient to form silica nanoparticles comprises incubating the silica precursors with a sufficient amount of a surfactant to form mesoporous silica nanoparticles.

24. The method of claim 20, wherein the surfactant is hexadecyl trimethylammonium bromide (CTAB).

25. The method of claim 23, further comprising loading a small-molecule drug on the negatively charged mesoporous silica nanoparticles, comprising incubating the negatively charged mesoporous silica nanoparticles with the small molecules drug in a solution, and sonicating the solution to load the small molecules drug on to the negatively charged mesoporous silica nanoparticles.

26. A method of administering a pharmaceutical agent to a subject, comprising
implanting a medical implant comprising the coated electrode of claim 13 in the subject, and
applying an electrical potential across the electrode to release the pharmaceutical agent from the mesoporous negatively charged silica nanoparticles in the coating to the subject.

27. The method of claim 26, wherein the electrical potential comprises a cyclic voltametric, sinusoidal, cosine wave, or square wave electrical stimulus.

28. A method of stimulating or recording an electrical signal in a subject, comprising:
implanting a medical implant comprising the coated electrode of claim 1 in the subject, and
stimulating or recording the electrical signal in the subject from the electrode in the implant.

29. A conductive polymer doped with negatively charged silica nanoparticles.

30. The conductive polymer of claim 29, wherein the conductive polymer is poly 3,4 ethylene dioxythiophene (PEDOT).

* * * * *